(12) United States Patent
Matsumoto

(10) Patent No.: US 7,182,753 B2
(45) Date of Patent: Feb. 27, 2007

(54) VALVE DISC AND COMBINATION FILLING DEVICE USING THE VALVE DISC, AND TUBE, PIPE JOINTING DEVICE, CONNECTION PORT MANUFACTURING DEVICE, AND PIPE JOINTING SYSTEM

(75) Inventor: Atsushi Matsumoto, Kanagawa (JP)

(73) Assignee: Terumo Kabushiki Kaisha, Tokyo (JP)

(*) Notice: Subject to any disclaimer, the term of this patent is extended or adjusted under 35 U.S.C. 154(b) by 0 days.

(21) Appl. No.: 10/312,010

(22) PCT Filed: Jun. 25, 2001

(86) PCT No.: PCT/JP01/05417

§ 371 (c)(1),
(2), (4) Date: Dec. 23, 2002

(87) PCT Pub. No.: WO01/97883

PCT Pub. Date: Dec. 27, 2001

(65) Prior Publication Data

US 2004/0059301 A1    Mar. 25, 2004

(30) Foreign Application Priority Data

Jun. 23, 2000    (JP) .............................. 2000-189166

(51) Int. Cl.
*A61M 5/14*    (2006.01)
(52) U.S. Cl. ........................................ 604/256; 604/34

(58) Field of Classification Search ..............................
604/167.01–167.06, 256, 236, 247, 201–206,
604/905, 244, 6.1, 9, 34, 99.03, 288.03
See application file for complete search history.

(56) References Cited

U.S. PATENT DOCUMENTS

| 4,610,665 A | 9/1986 | Matsumoto et al. |
| 4,673,393 A | 6/1987 | Suzuki et al. |
| 5,354,275 A | 10/1994 | Behnke et al. |
| 5,738,664 A | 4/1998 | Erskine et al. |

FOREIGN PATENT DOCUMENTS

| JP | 44-31039 | 12/1969 |
| JP | 2-949 B2 | 1/1990 |
| JP | 10-118178 A | 5/1998 |

*Primary Examiner*—Manuel Mendez
(74) *Attorney, Agent, or Firm*—Buchanan Ingersoll & Rooney PC

(57) ABSTRACT

A valve element including a pair of end faces, at least a part of which is constituted by an elastic material, characterized in that the valve element is provided with a first slit that is opened to a first end face and is not opened to a second end face of the pair of end faces, and a second slit that crosses with the first slit inside the valve element, is opened to the second end face and is not opened to the first end face, and the valve element is deformed such that inner surfaces of the second slit are brought into press contact with each other. This valve element is simple in structure, easy in operation, serviceable for a long period, and capable of preventing leakage of liquid surely.

25 Claims, 27 Drawing Sheets (a)  (b)

(a)  (b)

VALVE DISC AND COMBINATION FILLING DEVICE USING THE VALVE DISC, AND TUBE, PIPE JOINTING DEVICE, CONNECTION PORT MANUFACTURING DEVICE, AND PIPE JOINTING SYSTEM

TECHNICAL FIELD

The present invention relates to a valve element and a mixing and injecting device using the valve element, and a tube, a tube jointing device, a connection port manufacturing device, and a tube jointing system.

BACKGROUND ART

For example, there are known various medical instruments provided with a valve element such as a tube body guiding device for medical use that guides a tube body like a catheter for angiographies into a blood vessel.

Examples of a conventional valve element include a valve element consisting of a cylindrical elastic body in which a straight slit opened to (reaching) both end faces is formed, a valve element consisting of a cylindrical first elastic body in which a through-hole is formed and a cylindrical second elastic body in which a Y-shaped slit opened to both end faces is formed, and the like.

However, with the aforementioned valve element, the slit may open to form a gap between the slit and the tube body, causing leakage of liquid, particularly when the tube body is inserted and pulled out.

In addition, in the case in which the tube body is inserted for a long period, the valve element is deformed into a shape with the slit opened, whereby the slit does not close even after the tube body is pulled out and leakage of liquid is caused.

In order to suppress such leakage of liquid, a width of the slit only has to be reduced. However, if the width of the slit is reduced, a frictional resistance at the time when the tube body is inserted or pulled out increases, which makes operation for inserting or pulling out the tube body difficult.

Thus, in order to solve such a problem, a valve element consisting of a cylindrical elastic body is proposed in which a slit opened to (reaching) only one end face and a slit crossing with this slit in the inside of the valve element and opened to only the other end face (JP 2-949 B) are formed.

However, the aforementioned JP 2-949 B does not disclose an idea of deforming the valve element.

The inventor has found that, by deforming a valve element such that inner surfaces of one slit are brought into press contact with each other, liquid tightness can be increased and leakage of liquid can be prevented more surely without damaging operability of connection of a connector or the like.

It is a first object of the present invention to provide a valve element that is simple in structure, easy in operation, serviceable for a long period, and capable of preventing leakage of liquid surely.

In addition, on a site of medical care, at the time of an operation or at the time of hospital treatment, in the intravenous hyperalimentation, and the like, a catheter or a needle is inserted into a vein to perform infusion with drip injection.

In various types of infusion, in the case in which other drug solution or the like is injected, the injection is performed in parallel with the infusion or suspending the infusion. A method usually used as this method is to provide in advance a mixing and injecting section that is capable of connecting an infusion line or syringe of another route in the middle of an infusion route, and inject drug solution or the like via this mixing and injecting section.

As components used in this mixing and injecting section, there are kwon a rubber tube for mixing and injection, a liquid mixing and injecting device such as a Y site (also referred to as T-shaped tube) or a three-way cock, and a multiple cock (manifold) consisting of coupled three-way cocks.

In addition, a method also used in an artery line for the purpose of continuously monitoring an arterial pressure is to provide in advance a branching section having substantially the same action as the mixing and injecting section in the middle of the line and perform blood collection or the like from the branching section every time it is necessary.

Among the components used in the mixing and injecting section, the most primitive rubber tube for mixing and injection is pierced by a syringe with needle or the like and used. Thus, it is likely that a doctor or a nurse (hereinafter referred to as medical personnel) pricks his/her finger with the needle by mistake. In addition, if the rubber tube for mixing and injection is connected for a long period, there are problems in that drug solution (liquid) tends to leak easily, it is hard to secure in the case of mixing and injection for a long term, drug solution easily leaks when centesis is repeated (low in centesis resistance). However, the rubber tube for mixing and injection is still used currently because it is inexpensive.

In recent years, for the purpose of preventing pricking by mistake of medical personnel, a mixing and injecting port with valve has been developed which is provided with an open-closable valve of rubber in a mixing and injecting port and can be connected to a luer tip of a syringe or an extension tube without using a needle or can be connected using a blunt needle having an external diameter smaller than that of a luer tip.

However, in the aforementioned mixing and injecting port with valve, it is necessary to provide a slit communicating inner and outer faces of the valve therein, press the slit by a strong force to warp largely and close. Thus, the mixing and injecting port becomes complicated in structure and expensive. In addition, when it is used for a long period, the valve is deformed and the slit does not close sufficiently due to the deformation, thereby causing leakage of liquid. The mixing and injecting port with valve still has such a lot of problems.

In addition, a three-way cock usually has a structure of a female luer connector in a mixing and injecting section, and has an advantage in that it can be connected to a male luer connector of a syringe or an infusion line without using a needle. In addition, it has a function of switching an injection route such as injecting another drug solution simultaneously with injecting main drug solution or suspending injection of main drug solution to perform only side-injection. Thus, the three-way cock is used most frequently because it is convenient.

However, in the aforementioned three-way cock, there is a problem in that, if the cock is closed, since a part where drug solution does not flow (dead space) exists in the female luer and the female luer does not have a rubber septum for shutting the inside thereof from the outside, it is likely that fallen bacteria or the like in the air deposit on the female luer and, after connecting the female luer, the bacteria tend to propagate and contaminate a patient body.

Since there is a Y-shaped space for switching a flow path inside a cock of the three-way cock, if the three-way cock is closed in one direction, a part where drug solution does not easily flow is generated. If a few three-way cocks are connected in series to be used as a multiple cock, since there is a step in a connecting part, irregularity tends to occur in a flow of drug solution. Thus, there are inconveniences in that, when a small amount of drug solution is continuously injected accurately, the drug solution is diluted in the part where it does not easily flow or, when it is expected that the entire amount of drug solution is finished to be side-injected, the drug solution remains in the step or inside the cock and it takes time to flow the entire amount.

Moreover, since drug solution hardly spreads to such a part where drug solution does not easily flow, a step or a dead space, there is also a problem in that work for removing the air in a line before connecting an infusion line to a patient (priming) is made complicated.

The above-mentioned problems are the same for the conventional Y site to which a rubber septum is attached and a new mixing and injecting port that is improved such that a blunt needle or a male luer connector can be inserted for the purpose of preventing pricking by mistake of medical personnel.

It is a second object of the present invention to provide a mixing and injecting device that is simple in structure, capable of being operated easily and safely, serviceable for a long period, and capable of preventing leakage of liquid surely.

In addition, since the above-described mixing and injecting section is prepared in a number set in advance, there may not be the enough number of them.

In such a case, a port for side-injection that is not a main flow path must be additionally connected, which is time consuming. In addition, since liquid is not always flown to this port for side-injection, it is necessary to completely flow a remaining drug solution using, for example, saline or the like after drug solution is side-injected, which is time consuming and easily causes propagation of bacteria if the saline is stayed for a long time. Thus, it is likely that a large amount of propagated bacteria are injected into a patient when the drug solution is injected again.

It is a third object of the present invention to provide a tube that is simple in structure and in which a connection port can be easily provided, if necessary, a tube jointing device, a connection port manufacturing device, and a tube jointing system.

DISCLOSURE OF THE INVENTION

The above-mentioned first object is attained by first to thirteenth aspects of the present invention described below.

(1) A valve element including a pair of end faces, at least a part of which is constituted by an elastic material, characterized in that, the valve element is provided with a first slit that is opened to a first end face and is not opened to a second end face of the pair of end faces, and a second slit that crosses with the first slit inside the valve element, is opened to the second end face and is not opened to the first end face, and the valve element is deformed such that inner surfaces of the second slit are brought into press contact with each other.

(2) A valve element according to the aspect (1), wherein the first slit in the first end face and the second slit in the second end face are substantially perpendicular to each other.

(3) A valve element according to the aspect (1) or (2), wherein the valve element is plate-like, and the inner surfaces of the second slit are brought into press contact with each other by curving the valve element such that the first end face side thereof is protruded.

(4) A valve element according to the aspect (3), wherein a direction of the curving and a direction of the first slit in the first end face substantially coincide with each other.

(5) A valve element according to the aspect (3) or (4), wherein a direction perpendicular to the direction of the curving and a direction of the second slit in the second end face substantially coincide with each other.

(6) A valve element according to any one of the aspects (1) to (5), wherein the valve element is deformed such that inner surfaces of the first slit are brought into press contact with each other.

(7) A valve element according to any one of the aspects (1) to (6), wherein a compressing force is applied to the entire valve element.

(8) A valve element according to the aspect (1) or (2), wherein the valve element takes a tubular shape in which the first end face is an external peripheral surface and the second end face is an internal peripheral surface.

(9) A valve element according to the aspect (8), wherein a direction perpendicular to an axial direction of the valve element and a direction of the first slit in the first end face substantially coincide with each other.

(10) A valve element according to the aspect (8) or (9), wherein the axial direction of the valve element and a direction of the second slit in the second end face substantially coincide with each other.

(11) A valve element according to any one of the aspects (8) to (10), wherein an external shape in a cross section of the valve element after deformation is substantially circular.

(12) A valve element according to any one of the aspects (1) to (11), wherein the vicinity of the first slit on the first end face has a flat surface or a recessed surface.

(13) A valve element according to any one of the aspects (1) to (12), wherein the valve element includes a holding member for holding the valve element in a deformed state.

The above-mentioned second object is attained by fourteenth to thirty-fourth aspects of the present invention described below.

(14) A mixing and injecting device that has a valve element, at least a part of which is constituted by an elastic material, and a housing for holding the valve element, and is provided with a flow path in the inside thereof, which is characterized in that, the valve element has a first end face exposed to the outside and a second end face exposed to the inside of the flow path and is provided with a first slit, which is opened to the first end face and is not opened to the second end face, and a second slit, which crosses with the first slit in the inside thereof, opened to the second end face and is not opened to the first end face, and that the valve element is held by the housing in a state in which the valve element is deformed such that inner surfaces of the second slit are brought into press contact with each other.

(15) A mixing and injecting device according to the aspect (14), in which the first slit in the first end face and the second slit in the second end face are substantially perpendicular to each other.

(16) A mixing and injecting device according to the aspect (14) or (15), wherein a direction of the flow path and a direction of the second slit in the second end face substantially coincide with each other.

(17) A mixing and injecting device according to any one of the aspects (14) to (16), in which the valve element is plate-like, and the inner surfaces of the second slit are brought into press contact with each other by curving the valve element such that the first end face side of the valve element is protruded.

(18) A mixing and injecting device according to the aspect (17), in which a direction of the curving and a direction of the first slit in the first end face substantially coincide with each other.

(19) A mixing and injecting device according to the aspect (17) or (18), in which a direction perpendicular to the direction of the curving and a direction of the second slit in the second end face substantially coincide with each other.

(20) A mixing and injecting device according to any one of the aspects (14) to (19), in which the valve element is deformed such that inner surfaces of the first slit are brought into press contact with each other.

(21) A mixing and injecting device according to any one of the aspects (14) to (20), in which a compressing force is applied to the entire valve element.

(22) A mixing and injecting device according to any one of the aspects (14) to (16), wherein the valve element takes a tubular shape in which the first end face is an external peripheral surface and the second end face is an internal peripheral surface, and at least a part of the flow path is constituted by a lumen of the valve element.

(23) A mixing and injecting device according to the aspect (22), in which a direction perpendicular to an axial direction of the valve element and a direction of the first slit in the first end face substantially coincide with each other.

(24) A mixing and injecting device according to the aspect (22) or (23), in which the axial direction of the valve element and the direction of the second slit in the second end face substantially coincide with each other.

(25) A mixing and injecting device according to anyone of the aspects (22) to (24), wherein the valve element is deformed by being compressed in the direction substantially perpendicular to the axial direction of the valve element by the housing.

(26) A mixing and injecting device according to any one of the aspects (22) to (25), in which an external shape in a cross section of the valve element after deformation is substantially circular.

(27) A mixing and injecting device according to any one of the aspects (22) to (26), wherein:

the housing is tubular and has an opening on a side thereof, and the first slit is located in the opening;

the valve element is inserted in the housing; and the mixing and injecting device is constituted such that, when the opening is viewed from a direction of a straight line that passes a position deviated by 90° around a central axis of the valve element from a crossing section where the first slit and the second slit cross with each other and is perpendicular to the axial direction of the valve element, a part of the external peripheral surface of the valve element is seen from the opening.

(28) A mixing and injecting device according to any one of the aspects (22) to (26), wherein the housing includes a portion higher than an outer surface of a part where the first slit of the valve element exists, on an external peripheral side of the valve element and in the vicinity of the first slit.

(29) A mixing and injecting device according to any one of the aspects (22) to (26), wherein the housing includes a portion, which surrounds a part where the first slit of the valve element exists and is higher than an outer surface of the part where the first slit exists, on an external peripheral side of the valve element and in the vicinity of the first slit.

(30) A mixing and injecting device according to any one of the aspects (22) to (29), wherein engaging means for engaging the housing with the valve element is provided.

(31) A mixing and injecting device according to any one of the aspects (22) to (25), wherein the valve element is bent such that the lumen thereof is formed in a V-shape.

(32) A mixing and injecting device according to the aspect (31), wherein a crossing section where the first slit and the second slit cross with each other is substantially linear, a direction of the crossing section and an axial direction of the lumen on one side from a bent portion of the valve element substantially coincide with each other, and the lumen on one side is located on an extended line of the crossing section.

(33) A mixing and injecting device according to the aspect (31), wherein a crossing section where the first slit and the second slit cross with each other is substantially linear, and the crossing section and a central axis of the lumen on one side from a bent portion of the valve element substantially coincide with each other.

(34) A mixing and injecting device according to any one of the aspects (14) to (33), wherein the vicinity of the first slit on the first end face has a flat surface or a recessed surface.

The above-mentioned third object is attained by thirty-fifth to seventy-fifth aspects of the present invention described below.

(35) A tube including a flow path in the inside, at least a part of which is constituted by a flexible material, characterized in that, the tube is provided with at least one inner slit in a closed state or an opened state that reaches an internal peripheral (inner circumpherential) surface thereof and does not reach an external peripheral (outer circumpherential) surface thereof.

(36) A tube according to the aspect (35), wherein the inner slit is provided along an axis of the tube.

(37) A tube according to the aspect (35) or (36), wherein the tube includes position indicating means for indicating a position of the inner slit.

(38) A tube according to the aspect (37), in which the position indicating means is a guidepost provided along the inner slit.

(39) A tube according to any one of the aspects (35) to (38), in which at least one recessed portion or protruded portion is provided in an external peripheral part of the tube.

(40) A tube according to the aspect (39), in which the recessed portion or protruded portion is provided along the axis of the tube.

(41) A tube according to any one of the aspects (35) to (40), wherein a connection port is formed by forming an outer slit that crosses with the inner slit inside the tube, reaches the external peripheral (outer circumpherential) surface and does not reach the internal peripheral (inner circumpherential) surface.

(42) A tube according to the aspect (41), in which the outer slit and the inner slit are substantially perpendicular to each other.

(43) A tube jointing device characterized by including a tube according to any one of the aspects (35) to (40) and a housing that can be mounted on the tube.

(44) A tube jointing device according to the aspect (43), wherein the housing includes an opened portion from which at least a part of an external peripheral surface of the tube can be exposed.

(45) A tube jointing device according to the aspect (43) or (44), in which the housing is detachably attached to the tube.

(46) A tube jointing device according to any one of the aspects (43) to (45), in which the tube jointing device is constituted to be capable of mounting the housing in an arbitrary position in an axial direction and/or a peripheral direction of the tube.

(47) A tube jointing device according to any one of the aspects (43) to (46), in which the housing is constituted to be able to move in the axial direction and/or the peripheral direction of the tube.

(48) A tube jointing device according to any one of the aspects (43) to (47), wherein the housing is constituted such that the housing can bring the tube into a state in which inner surfaces of an inner slit are brought into press contact with each other.

(49) A tube jointing device according to any one of the aspects (43) to (48), in which at least one recessed portion or protruded portion is provided in an external peripheral part of the tube and a protruded portion or a recessed portion engaging with the at least one recessed portion or protruded portion is provided in the housing.

(50) A tube jointing device according to the aspect (49), in which the recessed portion or the protruded portion of the tube is provided along an axis of the tube.

(51) A tube jointing device according to any one of the aspects (43) to (50), wherein the tube jointing device includes position regulating means for regulating a position in at least a peripheral direction of the housing with respect to the tube.

(52) A tube jointing device according to any one of the aspects (43) to (51), in which a connection port is formed by forming in the tube an outer slit which crosses with the inner slit inside the tube, reaches the external peripheral (outer circumpherential) surface, and does not reach an internal peripheral (inner circumpherential) surface.

(53) A tube jointing device according to any one of the aspects (43) to (51), in which a connection port is formed by forming an outer slit which crosses with the inner slit inside the tube, reaches the external peripheral surface, and does not reach an internal peripheral surface, in a part located inside an opening part of the tube.

(54) A tube jointing device according to the aspect (52) or (53), in which the outer slit and the inner slit are substantially perpendicular to each other.

(55) A tube jointing device according to any one of the aspects (52) to (54), in which the housing has a function of regulating a position and/or a direction of the outer slit when the outer slit is formed.

(56) A tube jointing device according to any one of the aspects (52) to (55), in which the housing has a function of regulating a depth of the outer slit when the outer slit is formed.

(57) A connection port manufacturing device for forming a connection port in a tube according to any one of the aspects (35) to (42), characterized in that the connection port manufacturing device includes:
a tube holding section for detachably holding the tube; and
a cutter unit that is placed such that the cutter unit can be displaced with respect to the tube holding section and is provided with a blade, and
that the connection port manufacturing device is constituted such that the connection port is formed with the blade based on displacement of the cutter unit, by forming an outer slit which crosses with an inner slit inside the tube, reaches an external peripheral (outer circumpherential) surface and does not reach an internal peripheral (inner circumpherential) surface.

(58) A connection port manufacturing device according to the aspect (57), wherein the connection port manufacturing device is constituted so as to move the cutter unit in a direction substantially perpendicular to an axis of the tube with respect to the tube holding section and form the outer slit.

(59) A connection port manufacturing device according to the aspect (57) or (58) that includes regulating means having a function of regulating a position, a direction or a depth of the outer slit when the outer slit is formed.

(60) A connection port manufacturing device according to any one of the aspects (57) to (59), in which the tube holding section is constituted so as to be able to hold the tube in a state in which inner surfaces of the inner slit are brought into press contact with each other.

(61) A connection port manufacturing device according to any one of the aspects (57) to (60), in which the tube holding section is constituted so as to be able to hold the tube in an arbitrary position in an axial direction and/or a peripheral direction of the tube.

(62) A connection port manufacturing device according to any one of the aspects (57) to (61), in which the tube is constituted so as to be able to move in the axial direction and/or the peripheral direction of the tube with respect to the tube holding section.

(63) A connection port manufacturing device according to any one of the aspects (57) to (62) that is constituted so as to form the outer slit such that the outer slit and the inner slit are substantially perpendicular to each other.

(64) A connection port manufacturing device according to any one of the aspects (57) to (63), in which the tube holding section also serves as a housing that is mountable on the tube.

(65) A connection port manufacturing device according to the aspect (64), in which the housing is a housing according to any one of the aspects (43) to (56).

(66) A tube jointing system characterized by comprising:
a tube according to any one of the aspects (35) to (42); and
a blade for forming a connection port by forming in the tube an outer slit that crosses with an inner slit inside the tube, reaches an external peripheral (outer circumpherential) surface of the tube, and does not reach an internal peripheral (inner circumpherential) surface of the tube.

(67) A tube jointing system according to the aspect (66), comprising a connector that is connectable to the formed connection port.

(68) A tube jointing system characterized by including:
a tube according to the aspect (41) or (42); and
a connector that is connectable to the formed connection port.

(69) A tube jointing system characterized by including:
a tube jointing device according to any one of the aspects (43) to (56); and
a blade for forming a connection port by forming, in a tube of the tube jointing device, an outer slit that crosses with an inner slit inside the tube, reaches an external peripheral (outer circumpherential) surface of the tube, and does not reach an internal peripheral (inner circumpherential) surface of the tube.

(70) A tube jointing system according to the aspect (69) that includes a connector that is connectable to the formed connection port.

(71) A tube jointing system according to the aspect (70) that includes engaging means for engaging the connector with a housing.

(72) A tube jointing system characterized by including:
a tube jointing device according to any one of the aspects (52) to (56); and
a connector that is connectable to a formed connection port.

(73) A tube jointing system characterized in that the tube jointing system forms a connection port by deciding a position where a connector is connected to a tube according to any one of the aspects (35) to (42) or a tube jointing device according to any one of the aspects (43) to (56) and forming, in this position, an outer slit that crosses with an inner slit inside the tube, reaches an external peripheral (outer circumpherential) surface of the tube, and does not reach an internal peripheral (inner circumpherential) surface of the tube, and connects the connector to the formed connection port.

(74) A tube jointing system characterized in that the tube jointing system forms a plurality of connection ports by deciding a plurality of positions where a connector is connected to a tube according to any one of the aspects (35) to (42) or a tube jointing device according to any one of the aspects (43) to (56) and forming, in each of these positions, an outer slit that crosses with an inner slit inside the tube, reaches an external peripheral (outer circumpherential) surface of the tube, and does not reach an internal peripheral (inner circumpherential) surface of the tube, and connects the connector to a predetermined connection port among the formed plurality of connection ports.

(75) A tube jointing system according to the aspect (73) or (74) that includes engaging means for engaging the connector with a housing.

BEST MODE FOR IMPLEMENTING THE INVENTION

A valve element and a mixing and injecting device using the valve element, and a tube, a tube jointing device, a connection port manufacturing device, and a tube jointing system of the present invention will be hereinafter described in detail based on preferred embodiments shown in the accompanying drawings.

First, the valve element of the present invention and the mixing and injecting device using the valve element will be described.

Figure 1:
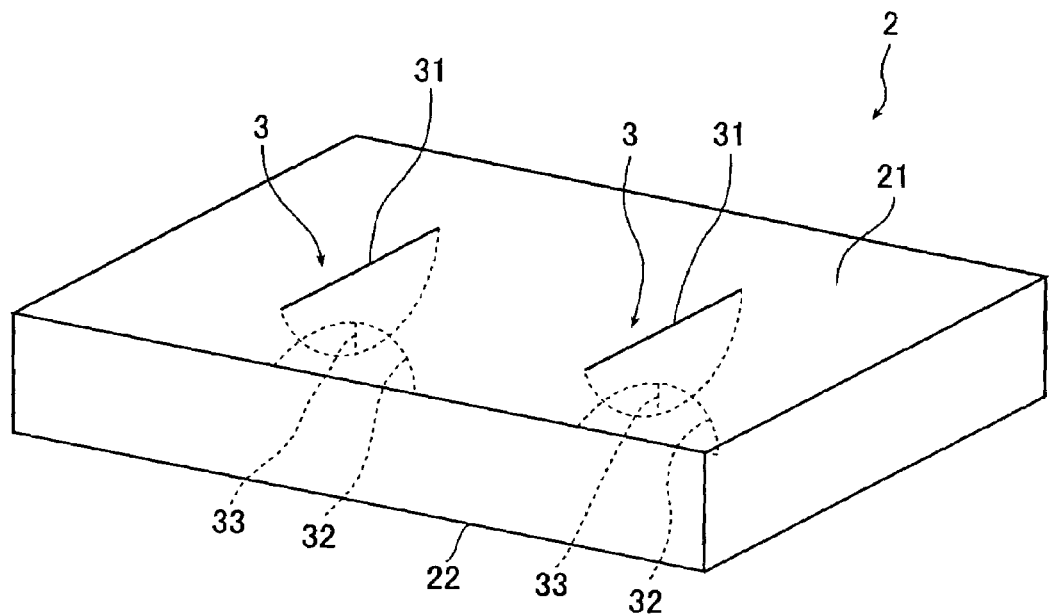
FIG. 1 is a perspective view showing a first embodiment (natural state) of a valve element of the present invention.
Figure 2:
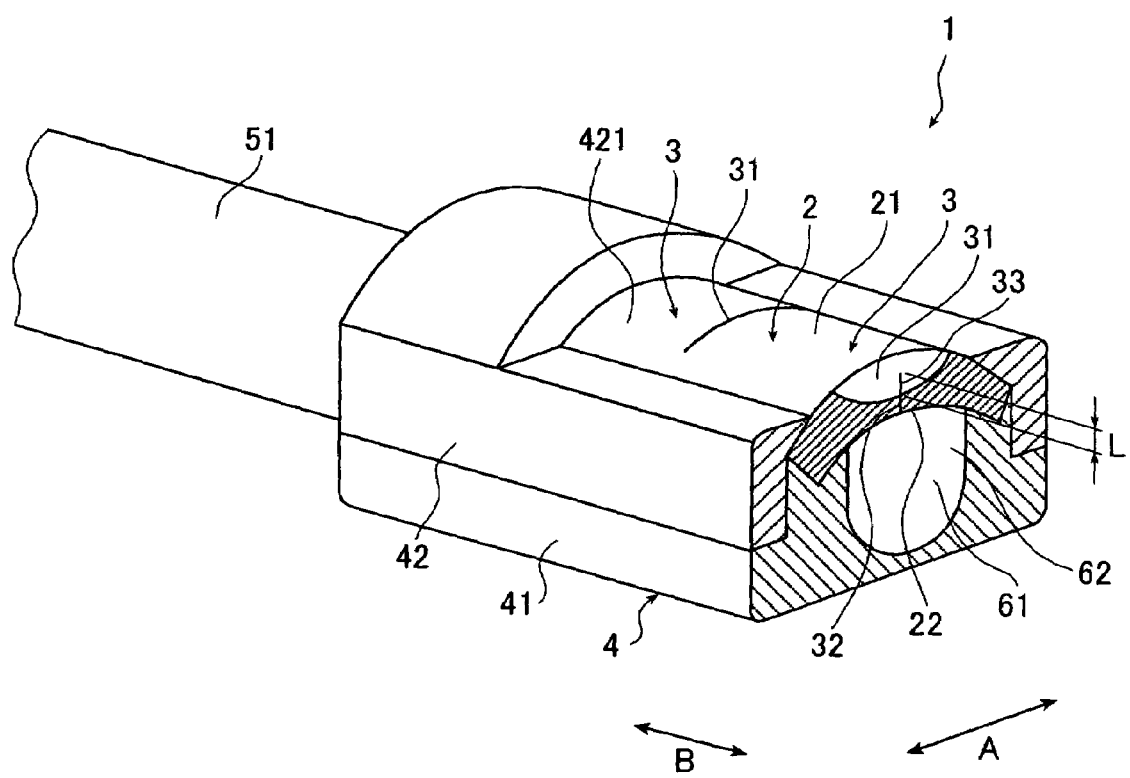
FIG. 2 is a perspective view showing a first embodiment of a mixing and injecting device of the present invention provided with the valve element shown in FIG. 1.

FIG. 1 is a perspective view showing a first embodiment (natural state) of the valve element of the preset invention. FIG. 2 is a perspective view showing a first embodiment of the mixing and injecting device of the present invention provided with the valve element shown in FIG. 1.

As shown in these figures, a valve element 2 is constituted by a plate-like elastic body. A shape of the valve element 2 in a natural state thereof, that is, a shape of the valve element 2 before it is mounted on a housing 4 discussed later is a substantially rectangular parallelepiped (tabular).

Here, the "natural state" refers to a state in which an external force is not applied to the valve element 2.

This valve element 2 includes two valve sections (mixing and injecting ports) 3 arranged in parallel along a direction (direction indicated by arrow B in FIG. 2) perpendicular to a direction of a curve of the valve element 2 discussed later (direction indicated by arrow A in FIG. 2), that is, a direction of a flow path 61 discussed later. Note that, since structures of these valve sections 3 are the same, one valve section 3 will be described representatively.

A first slit 31 and a second slit 32, which partially cross with each other in the inside of the valve section 3, are formed in the valve section 3, respectively.

The first slit 31 is opened to (reaches) one end face (first end face) 21 of a pair of end faces (surfaces) 21 and 22 (upper end face in FIG. 1) and is not opened to the other end face (second end face) 22 (lower end face in FIG. 1).

Conversely, the second slit 32 is opened to the second end face 22 and is not opened to the first end face 21.

These first slit 31 and second slit 32 cross with each other in a cross shape, that is, a crossing angle of the first slit 31 and the second slit 32 is 90° (the first slit 31 in the end face 21 and the second slit 32 in the end face 22 are perpendicular to each other). However, this crossing angle is not limited to 90°.

In addition, in the natural state, the first slit 31 and the second slit 32 are closed, respectively.

In addition, shapes of the first slit 31 and the second slit 32 are arc-shaped (substantially semicircular). However, it goes without saying that the first slit 31 and the second slit 32 are not limited to this shape.

In addition, in this embodiment, a crossing section 33 where the first slit 31 and the second slit 32 cross with each other is straight.

In addition, a length L of the crossing section 33 of the first slit 31 and the second slit 32 is not specifically limited, but is preferably in the order of 20 to 50% and more preferably in the order of 30 to 40% of a thickness of the valve element 2 (in particular, thickness of the valve section 3).

Further, the thickness of the valve element 2, in particular, the thickness of the valve section 3 is set to a thickness convenient for inserting the valve element 2 according to conditions such as an external diameter (diameter) and a length of a hard pipe (pipe body) to be inserted, a difference of pressures inside and outside the valve element 2, and a press contact force of the inner surfaces of the second slit 32. However, the thickness is preferably not less than 0.1 times and more preferably in the order of 0.3 to 1 time as large as the external diameter (diameter) of the hard pipe. In addition, in order to cope with a relatively large difference of pressures inside and outside the valve element 2, the thickness is preferably not less than two times as large as the external diameter (diameter) of the hard pipe.

Note that, although the thickness of the valve element 2 is uniform in this embodiment, it may not be uniform. For example, the thickness of the valve section 3 of the valve element 2 may be thicker or thinner than thickness of the other parts.

In addition, a Shore A hardness of the valve element 2 is preferably in the order of 20 to 80 and more preferably in the order of 30 to 50.

Further, an elongation percentage of a material constituting the valve element 2 is preferably larger and more preferably not less than 500%.

Examples of a material constituting the valve element 2 include elastic materials, for example, various kinds of rubbers such as natural rubber, isoprene rubber, butyl rubber, butadiene rubber, styrene-butadiene rubber, nitrile rubber, acrylic rubber, fluorine rubber, and silicone rubber, and various kinds of elastomers such as polyurethane, polyester, polyamide, olefin and styrene elastomers. One or more kinds of these materials can be mixed and used.

In order to manufacture the valve element 2, for example, a plate-like elastic body without the first slit 31 and the second slit 32 formed therein is formed, and the first slit 31 and the second slit 32 are formed in the obtained elastic body, respectively.

As shown in FIG. 2, a mixing and injecting device (liquid mixing and injecting device) 1 is constituted by the aforementioned valve element 2 and the hard housing (holding member) 4.

The housing 4 is constituted by a housing main body 41 and a cover member 42 in which an opening 421 is formed.

Examples of a material constituting this housing 4 include various kinds of resins such as polycarbonate, polysulphone, polyethylene, polypropylene, polystyrene, polyethylene terephthalate, polyethylene naphthalate, polyacrylate, polyamide, hard polyvinyl chloride, acrylonitrile-butadiene-styrene copolymer (ABS resin), cyclic polyolefin, fluoroplastic, and poly-(4-methylpentene-1), various kinds of metals such as stainless steel, aluminum, and titanium, various kinds of ceramics such as alumina, and a composite of these materials.

The valve element 2 is deformed (elastically deformed) such that the end face 21 becomes the outside and the end face 22 becomes the inside, and the inner surfaces of the second slit 32 are brought into press contact with each other, and the valve element 2 is nipped by the housing main body 41 of the housing 4 and the cover member 42 in that state (deformed state), thereby being secured to the housing 4 liquid-tightly. That is, the valve element 2 is held in the deformed state by the housing 4. Note that the valve sections 3 are placed in the position of the opening 421, respectively.

Here, "deformation" refers to a state in which at least a part of the valve element 2 changes into a different shape compared with a shape at the time when no external force is applied to the valve element 2 (including the case in which a shape is similar and a dimension changes).

In this embodiment, the valve element 2 is curved in a predetermined direction such that it is formed in a protruded shape on the outside thereof (upper side in FIG. 2), that is, a protruded shape on the end face 21 side, whereby the inner surfaces of the second slit 32 are brought into press contact with each other. In addition, the first slit 31 is closed.

A direction of the curving of the valve element 2 (direction indicated by arrow A in FIG. 2) is equal to (coincides with) the direction of the first slit 31 in the end face 21.

Consequently, the valve element 2 can be curved and the first slit 31 is kept in the closed state without applying an opening force to the first slit 31. Thus, cleaning work (e.g., cleaning of the end face 21 of the valve element 2) can be performed easily.

In addition, a direction perpendicular to the direction of the curving of the valve element 2 (direction indicated by arrow B in FIG. 2) and the direction of the second slit 32 in the end face 22 coincide with each other.

Consequently, the inner surfaces of the second slit 32 can be brought into press contact with each other surely.

Strength of press contact of the inner surfaces of the second slit 32 can be set in various ways by changing conditions such as a physical property of the valve element 2, a shape of a slit, and a degree of deformation.

In addition, a compressing force is preferably applied to the entire valve element 2.

Consequently, pressures applied to the first slit 31 and the second slit 32 (strength of press contact of the inner surfaces of the first slit 31 and press contact of the inner surfaces of the second slit 32) increases, respectively, and contamination by bacteria or the like can be prevented more surely.

Note that specific examples of deformation of a valve element include, other than the case in which the tabular valve element is curved, the case in which a curved plate-like valve element changes to tabular, the case in which a degree of curving of a curved plate-like valve element is increased or decreased, the case in which the curved plate-like valve element is curved in the opposite direction, and the case in which a compressing force or a tensile force is applied to the entirety or a part of a valve element.

One end side of a tube 51 is connected to this mixing and injecting device 1 on the left side thereof in FIG. 2 such that a lumen of the tube 51 and a hollow portion 62 of the mixing and injecting device 1 communicate with each other.

In addition, one end side of a not-shown tube is connected to the mixing and injecting device 1 on the right side thereof in FIG. 2 such that a lumen of the tube and the hollow portion 62 of the mixing and injecting device 1 communicate with each other.

Note that a main part of the flow path 61 is constituted by the hollow portion 62 of the mixing and injecting device 1, the lumen of the tube 51, and the lumen of the not-shown tube.

A direction of this flow path 61 (hollow portion 62) is equal to the direction of the second slit 32 in the end face 22 of the valve element 2, that is, the direction perpendicular to a direction of the curving of the valve element 2 (direction indicated by arrow B in FIG. 2).

An internal diameter (diameter) of the flow path 61 (hollow portion 62) is not specifically limited but is appropriately set according to an application and the like. However, it is preferably in the order of 1 to 20 mm that is a flow path diameter of a general liquid mixing and injecting device for medical use.

In addition, although not illustrated, in the end face 21 of the valve element 2, the vicinity of the first slit 31 (the end face 21 in the valve section 3) is preferably a flat surface or a recessed surface (e.g., curved recessed surface).

Consequently, when a hard pipe is inserted into the valve section 3, the insertion can be performed easily, rapidly and surely.

That is, since the end face 21 around the valve section 3 of the valve element 2 is a curved protruded surface (protruded surface) and only the end surface 21 in the valve section 3 is a flat surface or a recessed surface, a position of the valve section 3 can be grasped easily and surely. In addition, since the end face 21 in the valve section 3 is a flat surface or a recessed surface, a hard pipe is less likely to slip compared with the case in which the end face 21 is a protruded surface. Consequently, the hard pipe can be inserted into the valve section 3 easily.

Note that it goes without saying that the mixing and injecting device 1 can be used not only as a mixing and injecting port but also as a sampling port or a mixing and injecting and sampling port (mixing and injecting/sampling port), and the like.

Next, actions of the valve element 2 and the mixing and injecting device 1 will be described.

When, for example, a hard pipe (pipe body) or the like is not inserted in (inserted through) the valve section 3 of the valve element 2, as shown in FIG. 2, the first slit 31 and the second slit 32 are closed, respectively, and the inner surfaces of the second slit 32 are brought into press contact with each other. Consequently, liquid tightness (air tightness) of the flow path 61 is maintained.

If, for example, liquid (e.g., drug solution or the like) is side-injected (injected) in the flow path 61 (hollow portion 62) from another infusion line or syringe or liquid flowing through the flow path 61 is sampled, a not-shown predetermined hard pipe is inserted into the valve section 3.

When the hard pipe is inserted from the first slip 31 of the valve section 3, the inner surfaces of the crossing section 33 of the first slit 31 and the second slit 32 are brought into close adherence to an external peripheral surface of the hard pipe, and liquid tightness is maintained.

Then, when the hard pipe is inserted, the inner surfaces of the crossing section 33 are brought into close adherence to the external peripheral surface of the hard pipe, and liquid tightness is maintained. In this case, since the valve element 2 is curbed such that the inner surfaces of the second slit 32 are brought into press contact with each other, a width of an opening part of the second slit 32 is controlled to be minimum. Side-injection and sampling of the liquid are performed in this state.

After the side-injection and sampling of the liquid are finished, the hard pipe is pulled out from the valve section 3. In this case, liquid tightness is maintained as in the aforementioned case.

As described above, according to this valve element 2 (mixing and injecting device 1), the valve element 2 is curved (deformed) such that the inner surfaces of the second slit 32 are brought into press contact with each other. Thus, liquid tightness is secured and leakage of liquid from the valve element 2 can be prevented surely not only when nothing is inserted in (inserted through) the valve section 3 but also when, for example, a hard pipe is inserted in the valve section 3, when a hard pipe of a different external diameter is inserted in the valve section 3, or when a hard pipe is inserted into and pulled out from the valve section 3.

In addition, according to this mixing and injecting device 1, the smooth flow path 61 with little dead space or step where liquid tends to hold up is formed. Consequently, liquid flows smoothly and surely. That is, turbulence is less likely to occur, and liquid can be prevented from holding up.

In addition, when a syringe, a connector or the like is connected to the mixing and injecting device 1, since a hard pipe only has to be inserted into the valve section 3, the connecting operation can be performed easily and safely (connection operability is high).

Further, since the valve element 2 is curved (deformed) such that the inner surfaces of the second slit 32 are brought into press contact with each other, liquid tightness is secured and leakage of liquid from the valve element 2 can be prevented surely not only when nothing is inserted in (inserted through) the valve section 3 but also when, for example, a hard pipe is inserted in the valve section 3, when a hard pipe of a different external diameter is inserted in the valve section 3, or when a hard pipe is inserted into and pulled out from the valve section 3.

In addition, since the valve element 2 is curbed such that the inner surfaces of the second slit 32 are brought into press contact with each other, if a hard pipe is inserted for a long period, the valve element 2 is brought into a liquid tight state surely even after the hard pipe is pulled out, and leakage of liquid from the valve element 2 can be prevented surely. That is, durability is very high.

In addition, if a pressure in the flow path 61 rises and the valve element 2 is deformed such that an area (flow path area) in a cross section of the flow path 61 (hollow portion 62) increases, strength of press contact of the inner surfaces of the second slit 32 increases. Consequently, the liquid in the flow path 61 can be prevented from leaking from the valve element 2.

In addition, if a slight amount of liquid remains in the first slit 31 or the second slit 32, when the hard pipe is pulled out, the first slit 31 and the second slit 32 close, respectively, and the liquid holding up in the slits is completely discharged.

In addition, since the valve element 2 is curved such that the inner surfaces of the second slit 32 are brought into press contact with each other, leakage of liquid from the valve element 2 can be prevented even if a width of the first slit 31 or the second slit 32 is made relatively large.

Further, by making the width of the first slit 31 or the second slit 32 relatively large, a frictional resistance at the time of inserting a hard pipe and at the time of pulling it out can be made relatively small. Consequently, operations such as insertion and pulling out of the hard pipe can be performed more easily.

In addition, even if the inner surfaces of the first slit 31 or the second slit 32 are not in contact with the inserted hard pipe over the entire periphery thereof in the parts other than the crossing section 33, leakage of liquid from the valve element 2 can be prevented. Therefore, a deformation amount of the valve element 2 (the first slit 31 and the second slit 32) at the time when the hard pipe is inserted can be made relatively small. Consequently, if the hard pipe is inserted for a long period, the valve element 2 is brought into a liquid tight state surely even after the hard pipe is pulled out, and leakage of liquid from the valve element 2 can be prevented surely.

In addition, since the direction of the first slit 31 in the end face 21 of the valve element 2 is equal to the direction of curving of the valve element 2, the first slit 31 can maintain a closed state. Consequently, cleaning work (e.g., cleaning of the end face 21 of the valve element 2, etc.) can be performed easily.

In addition, since the direction of the second slit 32 in the end face 22 of the valve element 2 is equal to the direction of the flow path 61, when liquid flows along the flow path 61, a force in a direction of opening the second slit 32 does not act on the valve element 2. Consequently, the second slit 32 does not tend to open.

Further, even if the second slit 32 opens, since the direction of the second slit 32 in the end face 22 is equal to the direction of the flow path 61, liquid flows smoothly even in the second slit 32 and in the vicinity thereof. That is, turbulence does not tend to occur, and liquid can be prevented from holding up.

In addition, the valve element 2 is simple in structure.

In addition, by using the valve element 2, the mixing and injecting device 1 provided with the smooth flow path 61 with little dead space or step where liquid tends to hold up is realized.

In addition, since it is unnecessary to use a needle, there is an advantage that coring caused by cutting the valve element 2 with a point of a needle and leakage of liquid are prevented.

In addition, the mixing and injecting device 1 is simple in structure.

Note that, although the number of valve sections 3 of the valve element 2 is two in the aforementioned embodiment, the number of valve sections 3 of the valve element 2 may be one or three or more in the present invention. That is, the number of valve sections 3 of the valve element 2 may be singular or plural.

In addition, in the present invention, the valve element 2 may be constituted such that the first slit 31 is opened in the natural state and the first slit 31 closes after deformation. In this case, examples of the first slit 31 in the natural state include a groove or the like.

In addition, in the present invention, the valve element 2 may be constituted such that the second slit 32 is opened in the natural state and the inner surfaces of the second slit 32 are brought into press contact with each other after deformation. In this case, examples of the second slit 32 in the natural state include a groove or the like.

Further, in the present invention, the valve element 2 may be constituted such that, after deformation, the inner surfaces of the first slit 31 and the inner surfaces of the second slit 32 are brought into contact with each other, respectively. This embodiment (second example of the first embodiment) will be hereinafter described.

Figure 3:
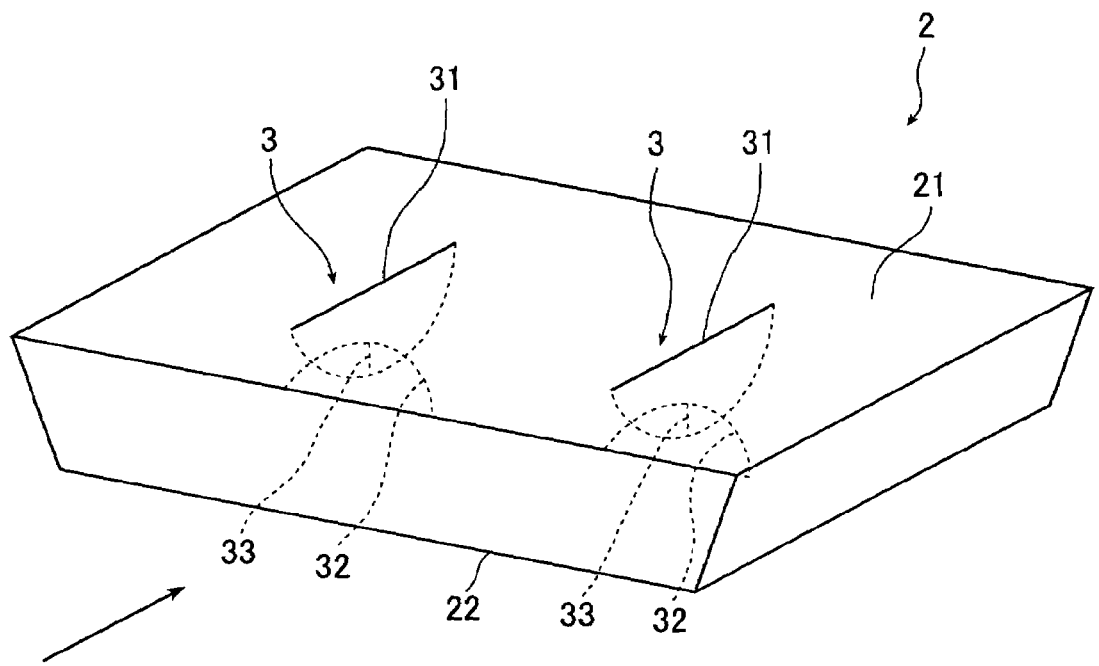
FIG. 3 is a perspective view showing a second example (natural state) of the first embodiment of the valve element of the present invention.

FIG. 3 is a perspective view showing the second example (natural state) of the first embodiment of the valve element of the present invention. Note that descriptions will be omitted regarding points common to the valve element of this embodiment and the valve element 2 of the aforementioned first embodiment, and main differences will be described.

As shown in the figure, the valve member 2 is constituted by a plate-like elastic body, and its shape (external shape) at the time when it is seen from a direction of an arrow in FIG. 3 in a natural state thereof, that is, its shape at the time when it is seen from the direction of the arrow in FIG. 3 before it is mounted on the housing 4 is substantially trapezoid.

In this case, a length of a side on the first end face 21 side of the trapezoid (upper side in FIG. 3) is set longer than a length of a side on the second end face 22 side (lower side in FIG. 3) (an area of the end face 21 is set larger than an area of the end face 22).

When the valve element 2 is mounted on the housing 4, the valve element 2 is curved, whereby the inner surfaces of the second slit 32 are brought into press contact with each other. In addition, the end face 21 side of the valve element 2 is compressed in a lateral direction in FIG. 3 by the housing 4, whereby the inner surfaces of the first slit 31 are brought into press contact with each other.

Consequently, contamination by bacteria or the like can be prevented more surely.

In addition, according to this valve element 2 (mixing and injecting device 1), the same effect as the valve element 2 (mixing and injecting device 1) of the aforementioned first embodiment is obtained.

Next, a second embodiment of the valve element of the present invention and a second embodiment of the mixing and injecting device of the present invention provided with the valve element will be described.

Figure 4:
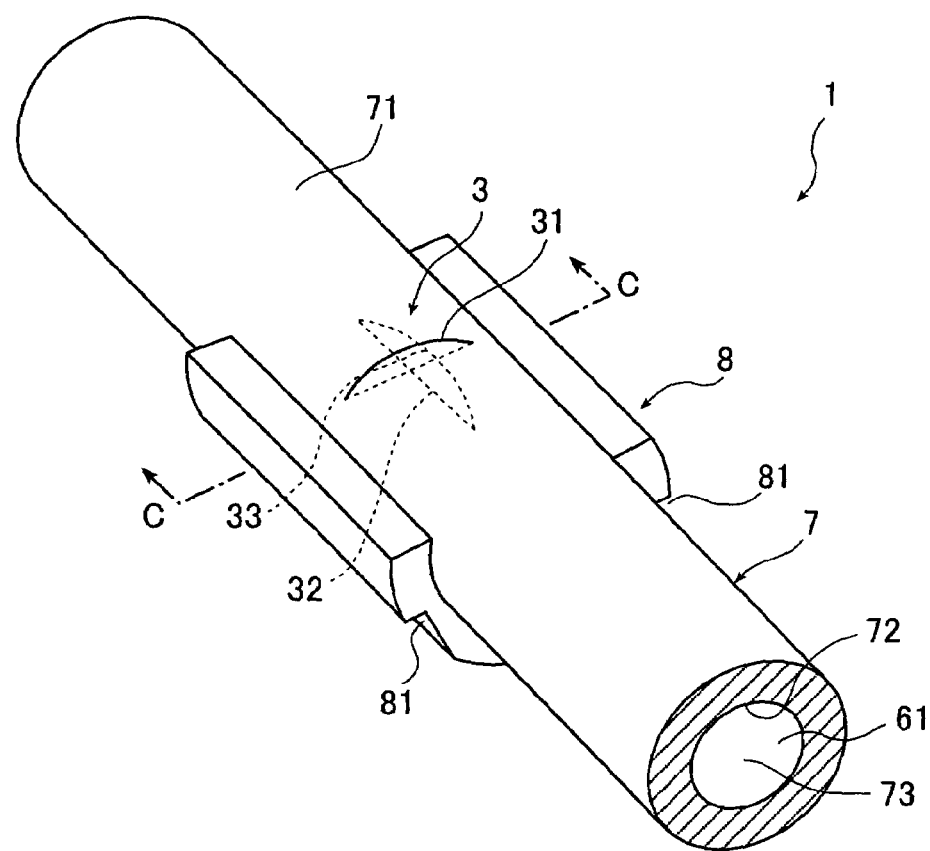
FIG. 4 is a perspective view showing a second embodiment of the valve element of the present invention and a second embodiment of the mixing and injecting device of the present invention provided with the valve element.
Figure 5:
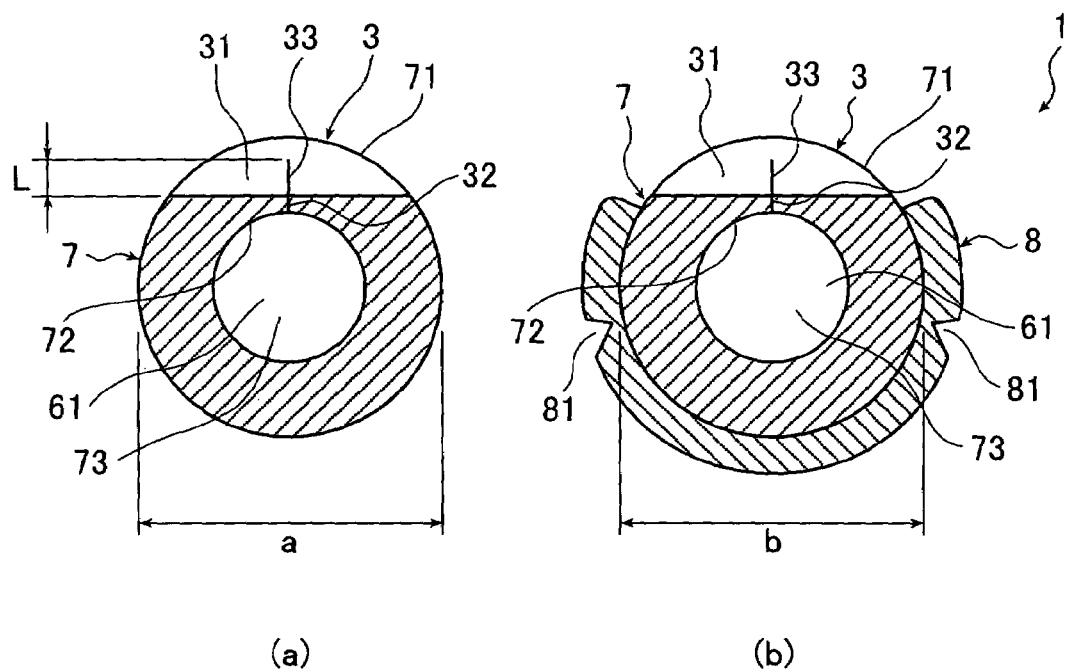
FIG. 5(*a*) is a transverse sectional view of the valve element in the natural state shown in FIG. 4, and FIG. 5(*b*) is a sectional view (transverse sectional view) taken along line C—C in FIG. 4.

FIG. 4 is a perspective view showing the second embodiment of the valve element of the present invention and the second embodiment of the mixing and injecting device of the present invention provided with the valve element. FIG. 5(*a*) is a transverse sectional view of the valve element in a natural state thereof shown in FIG. 4. FIG. 5(*b*) is a sectional view (transverse sectional view) along line C—C in FIG. 4. Note that descriptions will be omitted regarding points common to the valve element and the mixing and injecting device of this embodiment and the valve element 2 of the aforementioned first embodiment and the mixing and injecting device 1 of the aforementioned first embodiment, and main differences will be described.

As shown in these figures, a valve element 7 is constituted by a cylindrical (tubular) elastic body and has the valve section 3.

A first slit 31 of the valve section 3 is opened to an external peripheral surface (first end face) 71 of the valve element 7 and is not opened to an internal peripheral surface (second end face) 72.

Conversely, a second slit 32 of the valve section 3 is opened to the internal peripheral surface 72 of the valve element 7 and is not opened to the external peripheral surface 71.

Although shapes of the first slit 31 and the second slit 32 are arc-shaped (bow-shaped), it goes without saying that the first slit 31 and the second slit 32 are not limited to this shape.

In this valve element 7, a direction perpendicular to an axial direction thereof and a direction of the first slit 31 in the external peripheral surface 71 coincide with each other.

Consequently, the first slit 31 can be brought into a closed state, and cleaning work (e.g. cleaning of the external peripheral surface 71 of the valve element 7, etc.) can be easily performed.

In addition, the axial direction of the valve element 7 and a direction of the second slit 32 in the internal peripheral surface 72 coincide with each other.

Consequently, the inner surfaces of the second slit 32 can be brought into press contact with each other more surely.

Note that a part or a main part of the flow path 61 is constituted by a lumen 73 of the valve element 7. Therefore, a direction of this flow path 61 (lumen 73) is equal to the axial direction of the valve element 7, that is, the direction of the second slit 32 in the internal peripheral surface 72.

A shape of this valve element 7 in a natural state thereof, that is, a shape of the valve element 7 before it is mounted on a housing 8 is cylindrical as shown in FIG. 5(*a*).

In order to manufacture the valve element 7, for example, a cylindrical elastic body, in which the first slit 31 and the second slit 32 are not formed, is subjected to continuous extrusion molding, and the first slit 31 and the second slit 32 are formed in the obtained elastic body, respectively.

In order to form the second slit 32, for example, a cutter of a fixed blade length is inserted from one opening of the valve element 7, and the valve element 7 is cut from the internal peripheral surface 72 with the cutter.

In addition, in order to form the second slit 32, it is also possible to, for example, after forming the first slit 31, deform the valve element 7 such that the first slit 31 is opened, and the valve element 7 is cut from the opened first slit 31 toward the internal peripheral surface 72 with the cutter.

Further, in order to manufacture the valve element 7, it is also possible to, for example, form a cylindrical elastic body in which the first slit 31 is not formed and the second slit 32 is formed as a groove, and form the first slit 31 in the obtained elastic body. Even if the second slit 32 is opened in the natural state, the valve element 7 functions surely because it is deformed such that the inner surfaces of the second slit 32 are brought into press contact with each other.

As shown in FIG. 4, the mixing and injecting device 1 is constituted by the aforementioned valve element 7 and the hard housing (holding member) 8.

As shown in FIG. 5(*b*), a shape in a cross section of the housing 8 is C-shaped. That is, the entire shape of the housing 8 is a shape with the upper side of the cylinder in FIG. 4 and FIG. 5 removed.

A pair of grooves 81 and 81 are formed along an axial direction of the housing 8 in an external peripheral part of this housing 8. When a not-shown connector is connected to the mixing and injecting device 1, a pair of pawls of the connector engages with the pair of grooves 81 and 81, whereby disengagement of the connector from the mixing and injecting device 1 is prevented.

As shown in FIG. 5(*b*), the valve element 7 is inserted into the housing 8 such that the valve section 3 is on the upper side in FIG. 5, the external peripheral surface 71 of the valve section 3 is exposed, and the valve section 3 is located in the position of the housing 8, and is nipped by the housing 8.

That is, when the crossing section 33 of the first slit 31 and the second slit 32 are placed on the upper side (upside) in FIG. 5, the valve element 7 is pressed by a corresponding portion of the housing 8 from its side (pressed in a direction substantially perpendicular to the axial direction of the valve element 7), thereby being deformed such that the inner surfaces of the second slit 32 are brought into press contact with each other (slightly squashed in a lateral direction in FIG. 5), and held in the deformed state by the housing 8.

An external shape and an internal shape of this valve element 7 in its cross section after the deformation, that is, an external shape and an internal shape in its cross section in the state in which it is mounted on the housing 8 are substantially circular, respectively.

Note that an external diameter (diameter) "a" in a natural state of the valve element 7 shown in FIG. 5(*a*) and an internal diameter (diameter) "b" of the housing 8 shown in FIG. 5(*b*) are set such that the external diameter "a" is larger than the internal diameter "b", respectively.

For example, one end side of a not-shown tube is connected to a left side in FIG. 4 of this mixing and injecting device 1 such that a lumen of the tube and the lumen 73 of the valve element 7 communicate with each other. In addition, for example, one end side of a not-shown tube is connected to a right side in FIG. 4 such that a lumen of the tube and the lumen 73 of the valve element 7 communicate with each other. In this case, the main part of the flow path 61 is constituted by the lumen 73 of the valve element 7 and the lumens of the tubes.

In addition, this valve element 7 can do without the aforementioned tubes by adjusting its length in the axial direction (making it relatively long). That is, the main part of the flow path 61 can be constituted by the lumen 73 of the valve element 7.

According to this valve element 7 (mixing and injecting device 1), the same effect as the valve element 2 (mixing and injecting device 1) of the aforementioned first embodiment is obtained.

Further, since this valve element 7 is cylindrical, the flow path 61 smoother than that of the valve element 2 of the aforementioned first embodiment is formed. That is, by using the valve element 7, the mixing and injecting device 1 provided with the smooth flow path 61 without a dead space or a step where liquid tends to hold up is realized.

In addition, since the valve element 7 is cylindrical, it functions surely even if the second slit 32 is formed in a shape for allowing it to open in the natural state (e.g., groove) or the valve element 7 is decentered or slightly squashed.

Note that, although the number of valve sections 3 of the valve element 7 is one (single) in the aforementioned embodiment, the number of valve sections 3 of the valve element 7 may be two or more (plural) in the present invention.

In addition, the valve element 7 may be adhered to the housing 8 with, for example, an adhesive.

In addition, a flat part may be provided on the external peripheral side of the housing 8 such that stability is increased.

Further, a connection port connected to the end of the valve element 7 for connecting another liquid delivery device may be provided.

Next, a third embodiment of the valve element of the present invention will be described.

Figure 6:
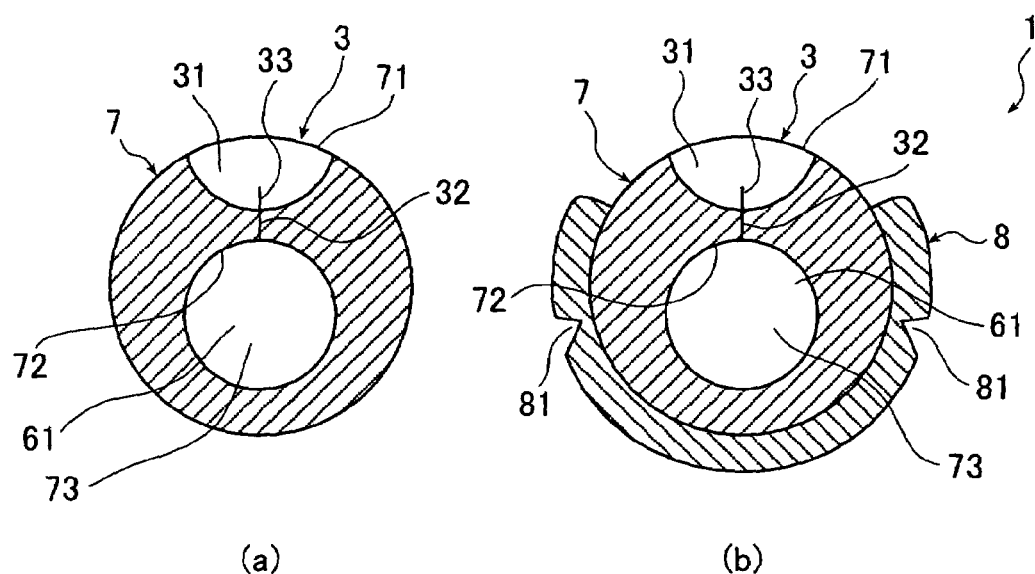
FIG. 6(*a*) is a transverse sectional view showing a third embodiment (natural state) of the valve element of the present invention, and FIG. 6(*b*) is a transverse sectional view showing a third embodiment of the mixing and injecting device of the present invention provided with the valve element shown in FIG. 6(*a*).

FIG. 6(*a*) is a transverse sectional view showing the third embodiment (natural state) of the valve element of the present invention. FIG. 6(*b*) is a transverse sectional view showing a third embodiment of the mixing and injecting device of the present invention provided with the valve element shown in FIG. 6(*a*). Note that descriptions will be omitted regarding points common to the valve element of this embodiment and the valve element 7 of the aforementioned second embodiment, and main differences will be described.

As shown in the figures, the valve element 7 is constituted by a cylindrical (tubular) elastic body in which the lumen 73 is decentered. That is, a thickness (wall thickness) of the valve element 7 is not uniform.

Further, in this valve element 7, the valve section 3, that is, the first slit 31 and the second slit 32 are arranged in a position where the thickness of the valve element 7 is largest.

In other words, the thickness of the valve element 7 is set such that a thickness of the valve section 3, that is, a thickness of a part where the first slit 31 and the second slit 32 are placed becomes largest.

According to this valve element 7 (mixing and injecting device 1), the same effect as the valve element 7 (mixing and injecting device 1) of the aforementioned second embodiment is obtained.

Further, in this valve element 7 (mixing and injecting device 1), since the thickness of the valve section 3 is largest, liquid tightness is maintained more surely, withstand pressure is higher, and leakage of liquid from the valve element 7 can be prevented more surely compared with the valve element 7 (mixing and injecting device 1) of the aforementioned second embodiment.

Next, a fourth embodiment of the valve element of the present invention will be described.

Figure 7:
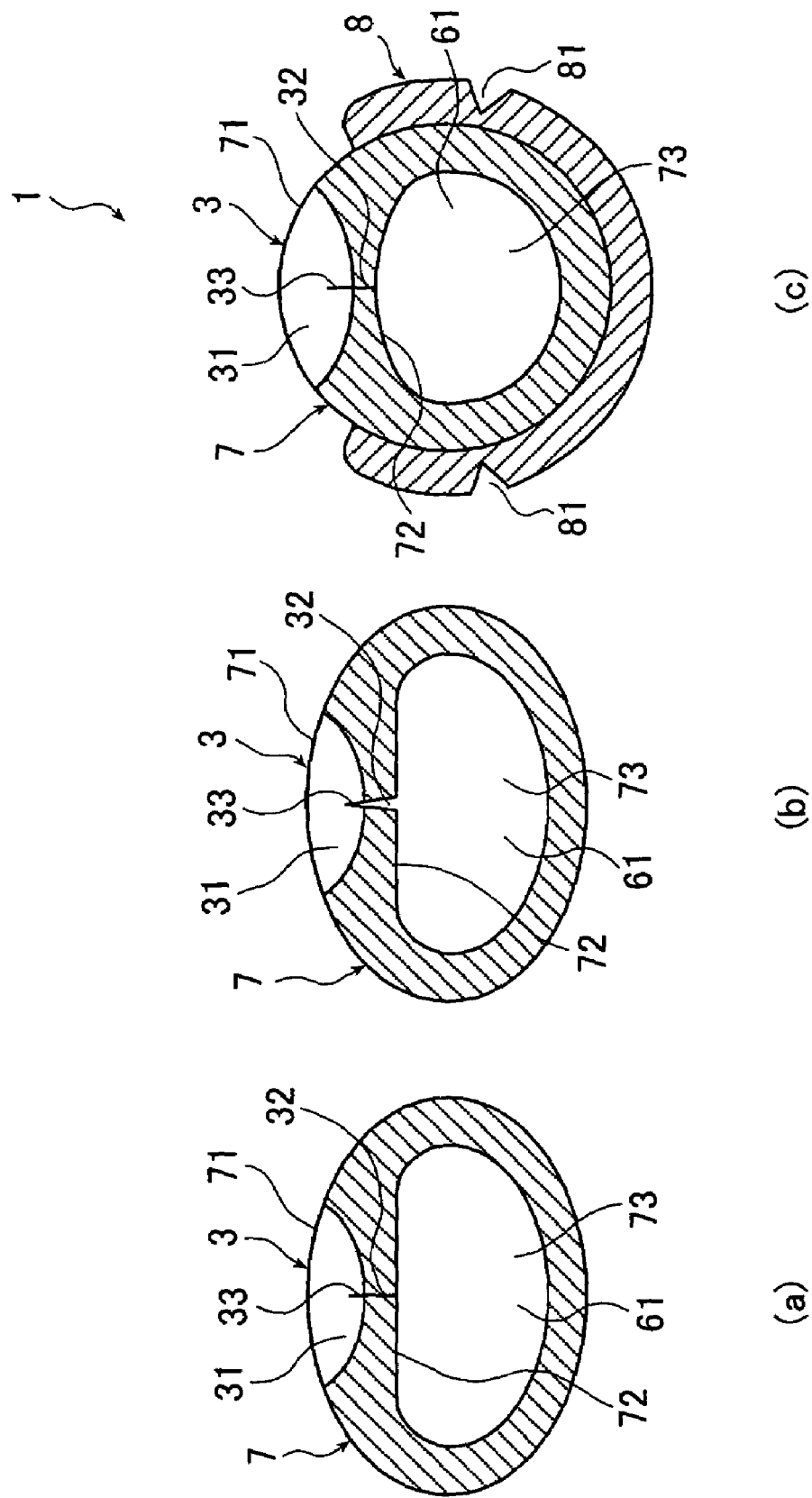
FIG. 7(*a*) and FIG. 7(*b*) are transverse sectional views showing a fourth embodiment (natural state) of the valve element of the present invention, respectively, and FIG. 7(*c*) is a transverse sectional view showing a fourth embodiment of the mixing and injecting device of the present invention provided with the valve element shown in FIG. 7(*a*) or FIG. 7(*b*).

FIG. 7(*a*) and FIG. 7(*b*) are transverse sectional views showing the fourth embodiment (natural state) of the valve element of the present invention, respectively. FIG. 7(*c*) is a transverse sectional view showing a fourth embodiment of a mixing and injecting device of the present invention provided with the valve element shown in FIG. 7(*a*) or FIG. 7(*b*). Note that descriptions will be omitted regarding points common to the valve element of this embodiment and the valve element 7 of the aforementioned second embodiment, and main differences will be described.

As shown in the figures, the valve element 7 is constituted by a tubular elastic body.

An external shape of this valve element 7 in its cross section in a natural state thereof, that is, an external shape in the cross section before it is mounted on the housing 8 is substantially elliptical as shown in FIG. 7(*a*) and FIG. 7(*b*).

In addition, an internal shape of the valve element 7 in its cross section in a natural state thereof, that is, an internal shape in the cross section before it is mounted on the housing 8 is substantially semicircular as shown in FIG. 7(*a*) and FIG. 7(*b*).

Further, an external shape of the valve element 7 in its cross section after deformation, that is, an external shape in the cross section in the state in which it is mounted on the housing 8 is substantially elliptical as shown in FIG. 7(*c*).

In addition, an internal shape of the valve element 7 in its cross section after deformation, that is, an internal shape in the cross section in the state in which it is mounted on the housing 8 is substantially circular as shown in FIG. 7(*c*).

Further, a thickness (wall thickness) of the valve element 7 is not uniform, and the valve section 3, that is, the first slit 31 and the second slit 32 are arranged in a position where the thickness of the valve element 7 is largest.

In other words, the thickness of the valve element 7 is set such that a thickness of the valve section 3, that is, a thickness of a part where the first slit 31 and the second slit 32 are located becomes largest.

In the valve element 7 shown in FIG. 7(*a*), the second slit 32 is closed in the natural state.

In addition, in the valve element 7 shown in FIG. 7(*b*), the second slit 32 is opened in the natural state. That is, the second slit 32 in the natural state is a V-shaped groove.

As described above regarding both the valve element 7 shown in FIG. 7(*a*) and the valve element 7 shown in FIG. 7(*b*), after deformation, that is, in the state in which the valve element 7 is mounted on the housing 8, the inner surfaces of the second slit 32 are brought into press contact with each other by the deformation as shown in FIG. 7(*c*).

According to this valve element 7 (mixing and injecting device 1), the same effect as the valve element 7 (mixing and injecting device 1) of the aforementioned second embodiment is obtained.

In addition, in this valve element 7 (mixing and injecting device 1), since the external shape in the cross section is changed from a substantially elliptical shape to a substantially circular shape, liquid tightness is maintained more surely, withstand pressure is higher, and leakage of liquid from the valve element 7 can be prevented more surely compared with the valve element 7 (mixing and injecting device 1) of the aforementioned second embodiment.

In addition, since the thickness of the valve section 3 is largest, liquid tightness is maintained more surely, withstand pressure is higher, and leakage of liquid from the valve element 2 can be prevented more surely compared with the valve element 7 (mixing and injecting device 1) of the aforementioned second embodiment.

Next, a fifth embodiment of the valve element of the present invention will be described.

Figure 8:
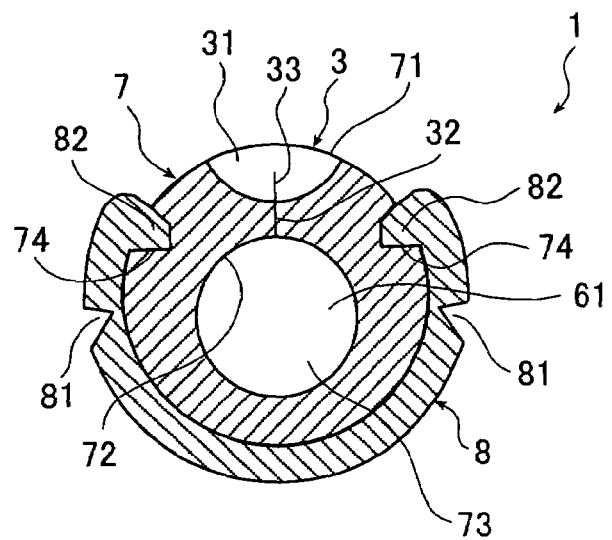
FIG. 8 is a transverse sectional view showing a fifth embodiment of the valve element of the present invention and a fifth embodiment of the mixing and injecting device of the present invention provided with the valve element.

FIG. 8 is a transverse sectional view showing the fifth embodiment of the valve element of the present invention and a fifth embodiment of a mixing and injecting device of the present invention provided with the valve element. Note that descriptions will be omitted regarding points common to the valve element of this embodiment and the valve element 7 of the aforementioned third embodiment, and main differences will be described.

As shown in the figure, a pair of grooves 74 and 74 are formed along an axial direction of the valve element 7 in the external peripheral part of the valve element 7.

Further, a pair of ribs (protruded shape) 82 and 82 that can engage with the pair of grooves 74 and 74 are formed in a position in the internal peripheral part on the upper side in FIG. 8 of the housing 8 corresponding to the pair of grooves 74 and 74.

Consequently, rotation (displacement) of the valve element 7 with respect to the housing 8, disengagement of the valve element 7 from the housing 8, and the like can be prevented.

Note that engaging means (disengagement preventing means) is constituted by the pair of grooves 74 and 74 and the pair of ribs 82 and 82.

According to this valve element 7 (mixing and injecting device 1), the same effect as the valve element 7 (mixing and injecting device 1) of the aforementioned third embodiment is obtained.

Further, since the grooves 74 are provided in this valve element 7 and the ribs 82 that can engage with the grooves 74 are provided in the housing 8, rotation (displacement) of the valve element 7 with respect to the housing 8, disengagement of the valve element 7 from the housing 8, for example, disengagement of the valve element 7 from the housing 8 at the time when an inserted hard pipe is pulled out, and the like can be prevented.

In addition, in this valve element 7, the valve element 7 can be mounted on the housing 8 easily compared with the case in which a valve element and a housing are adhered to each other with an adhesive. That is, the mixing and injecting device 1 can be manufactured (assembled) easily.

Note that, in the present invention, grooves may be provided in the housing 8 and ribs that can engage with the grooves may be provided in the valve element 7.

In addition, in the present invention, the engaging means is not limited to a combination of grooves and ribs, and examples of the engaging means include a combination of recessed portions and protruded portions, a combination of grooves and protruded portions, and the like in addition to the combination of grooves and ribs.

Next, a sixth embodiment of the valve element of the present invention will be described.

Figure 9:
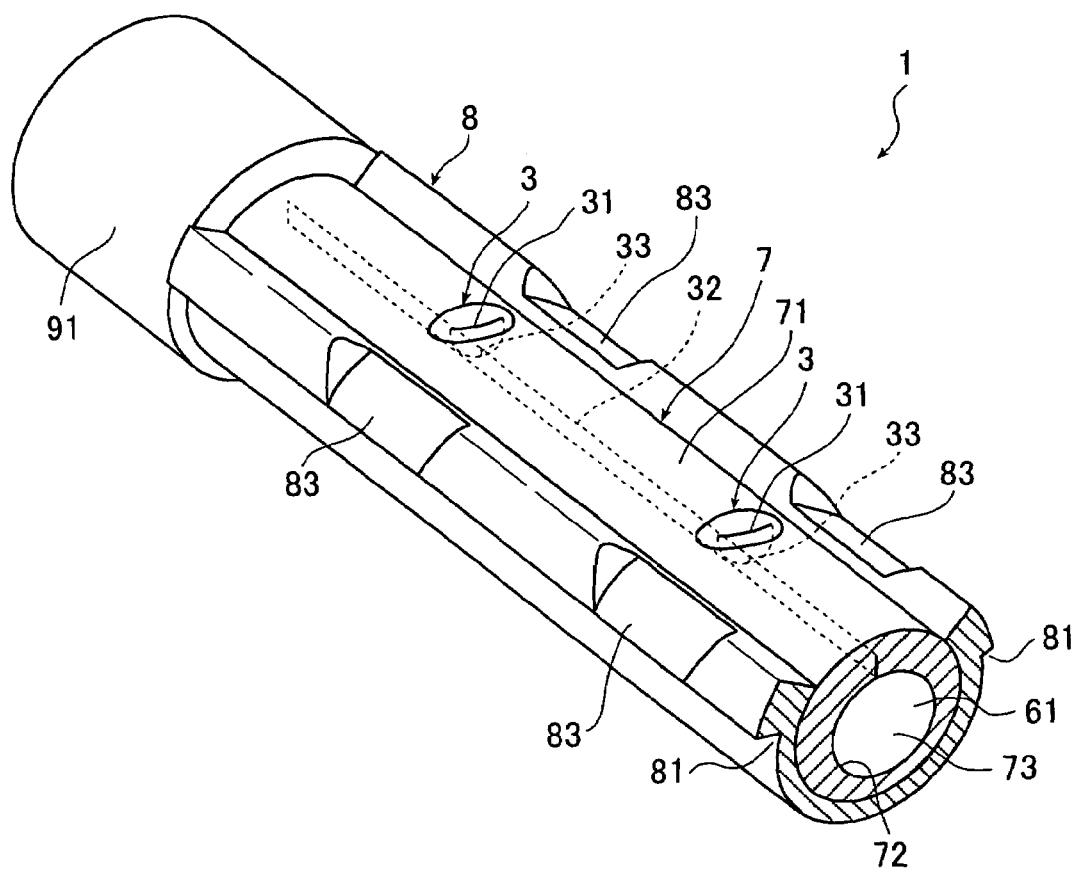
FIG. 9 is a perspective view showing a sixth embodiment of the valve element of the present invention and a sixth embodiment of the mixing and injecting device of the present invention provided with the valve element.

FIG. 9 is a perspective view showing the sixth embodiment of the valve element of the present invention and a sixth embodiment of a mixing and injecting device of the present invention provided with the valve element. Note that descriptions will be omitted regarding points common to the valve element of this embodiment and the valve element 7 of the aforementioned third embodiment, and main differences will be described.

As shown in the figure, the valve element 7 has two valve sections 3 that are arranged in parallel along an axial direction of the valve element 7, that is a direction of the flow path 61 (lumen 73).

In this case, the second slit 32 of the two valve sections 3 is constituted by a common one (one streak of) slit extending along the axial direction of the valve element 7.

Consequently, since only one second slit 32 has to be formed in manufacturing the valve element 7 having a plurality of (two in this embodiment) valve sections 3, manufacturing is easy and productivity is high.

Note that, as described above, this second slit 32 may be closed or may be opened in the natural state. In both cases, the valve element 7 is deformed and the inner surfaces of the second slit 32 are brought into press contact each other in the state in which the valve element 7 is mounted on the housing 8.

In addition, in the external peripheral surface 71 of the valve element 7, the vicinity of the first slit 31 (the external peripheral surface 71 in the valve section 3) is a flat surface or a recessed surface. Note that, in this embodiment, the external peripheral surface 71 in the valve sections 3 is a curved recessed surface as shown in FIG. 9.

Consequently, when a hard pipe is inserted into the valve section 3, the insertion can be performed easily, rapidly and surely.

That is, since the external peripheral surface 71 around the valve sections 3 of the valve element 7 is a curved protruded surface (protruded surface) and only the external peripheral surface 71 in the valve sections 3 is a flat surface or a recessed surface, positions of the valve sections 3 can be grasped easily and surely. In addition, since the external peripheral surface 71 in the valve sections 3 is a flat surface or a recessed surface, a hard pipe is less likely to slip compared with the case in which the external peripheral surface 71 is a protruded surface. Consequently, the hard pipe can be inserted into the valve section 3 easily.

In addition, cutout portions 83 are formed as a guidepost indicating positions of the valve sections 3 in a part corresponding to each valve section 3 in the part on the upper side in FIG. 9 of the housing 8, respectively.

Consequently, the positions of the valve sections 3 can be grasped easily and surely.

Note that, as described above, since the external peripheral surface 71 in the valve sections 3 is made as a flat surface or a recessed surface and the external peripheral surface 71 becomes a guidepost for indicating the positions of the valve sections 3, it goes without saying that the cutout portions 83 may be eliminated.

In addition, for example, one end side of a not-shown tube is connected to a left side in FIG. 9 of this mixing and injecting device 1 such that a lumen of the tube and the lumen 73 of the valve element 7 communicate with each other via a coupling portion 91. In addition, for example, one end side of a not-shown tube is connected to a right side in FIG. 9 such that a lumen of the tube and the lumen 73 of the valve element 7 communicate with each other via a not-shown coupling portion.

According to this valve element 7 (mixing and injecting device 1), the same effect as the valve element 7 (mixing and injecting device 1) of the aforementioned third embodiment is obtained.

Further, in this valve element 7 (mixing and injecting device 1), the vicinity of the first slit 31 of the external peripheral surface thereof (the external peripheral surface 71 in the valve sections 3) is a flat surface or a recessed surface. Thus, when a hard pipe is inserted into the valve sections 3, the insertion can be performed easily, rapidly and surely.

Note that, in the mixing and injecting devices 1 of the aforementioned second to fifth embodiments and seventh and eighth embodiments discussed later, the vicinity of a first slit in an external peripheral surface (first end face) of a valve element is preferable made as a flat surface or a recessed surface (e.g., curved recessed surface), respectively, as in the mixing and injecting device 1 of this sixth embodiment. Consequently, when a hard pipe (pipe body) is inserted into a valve section, the insertion can be performed easily, rapidly and surely.

Next, a seventh embodiment of the mixing and injecting device of the present invention will be described.

Figure 10:
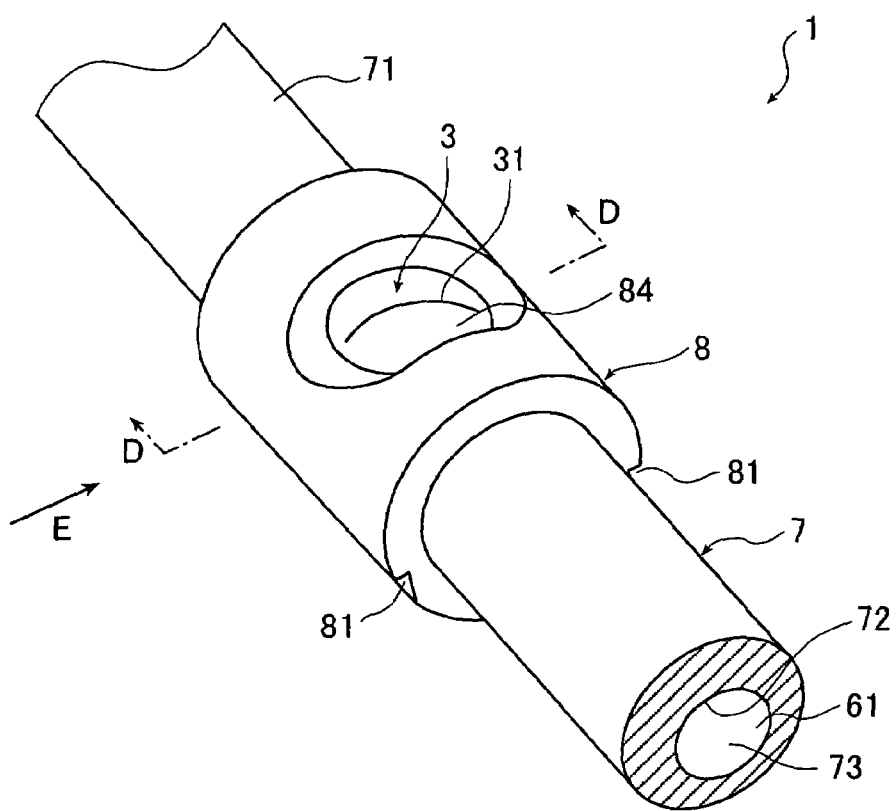
FIG. 10 is a perspective view showing a seventh embodiment of the mixing and injecting device of the present invention.
Figure 11:
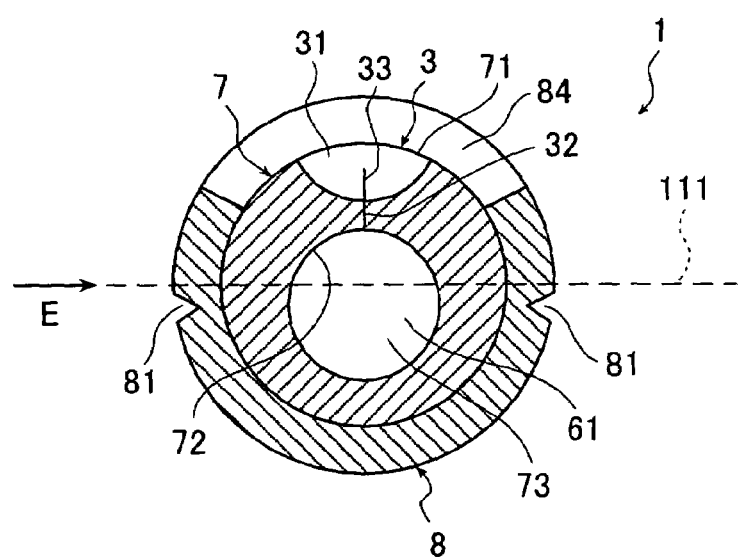
FIG. 11 is a sectional view (transverse sectional view) taken along line D—D in FIG. 10.
Figure 12:
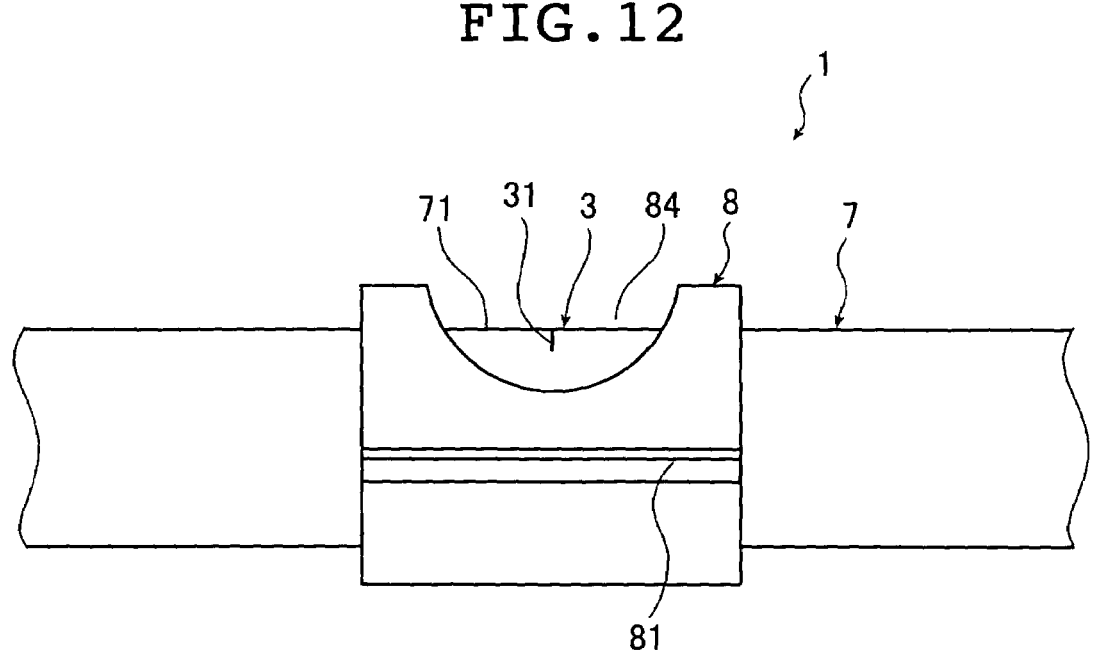
FIG. 12 is a side view of the mixing and injecting device shown in FIG. 10.

FIG. 10 is a perspective view showing the seventh embodiment of the mixing and injecting device of the present invention. FIG. 11 is a sectional view (transverse sectional view) along line D—D in FIG. 10. FIG. 12 is a side view of the mixing and injecting device shown in FIG. 10. Note that descriptions will be omitted regarding points common to the mixing and injecting device of this embodiment and the mixing and injecting device 1 of the aforementioned third embodiment, and main differences will be described.

As shown in these figures, the housing 8 of the mixing and injecting device 1 is cylindrical (tubular).

An opening 84 is formed on the side of the housing 8 and in an intermediate part in an axial direction thereof.

The valve element 7 is inserted in the housing 8 and is held in the housing 8 in the state in which the valve element 7 is deformed such that the inner surfaces of the second slit 32 are brought into press contact with each other.

In this case, the valve section 3 (first slit 31) of the valve element 7 is located in this opening 84, and the external peripheral surface 71 of the valve section 3 (the external peripheral surface 71 in the vicinity of the first slit 31) is exposed from the opening 84.

FIG. 12 shows the mixing and injecting device 1 at the time when it is viewed from a direction indicated by arrow E in FIG. 10 and FIG. 11, that is, the mixing and injecting device 1 at the time when it is viewed from a direction of a straight line 111, which passes a position deviating by 90° around a central axis of the valve element 7 from the crossing section 33 of the first slit 31 and the second slit 32 shown in FIG. 11 and which is perpendicular to an axial direction of the valve element 7.

Conditions such as a shape and a dimension of the opening 84 of the housing 8 are set such that, when the opening 84 is viewed from a direction of the straight line 111 (direction indicated by arrow E in FIG. 10 and FIG. 11), a part of the external peripheral surface 71 of the valve element 7 is seen from the opening 84 as shown in FIG. 12.

Consequently, in the opening 84 of the housing 8, for example, alcohol cotton or the like is slid in a lateral direction in FIG. 11, that is, along the external peripheral surface 71 of the valve element 7, whereby the external peripheral surface 71 of the valve section 3 of the valve element 7 (the external peripheral surface 71 in the vicinity of the first slit 31) can be wiped easily and surely and can be cleaned.

In this case, since a direction of the first slit 31 and a moving direction of the alcohol cotton substantially coincide with each other, the first slit 31 does not substantially become a resistance, a force in a direction for opening the first slit 31 does not act, and the first slit 31 can maintain the closed state.

In addition, since the housing 8 is cylindrical and the valve element 7 is inserted in the housing 8, the external peripheral surface 71 of the valve section 3 of the valve element is placed on a central axis side (internal peripheral side) of the housing 8 with respect to an external peripheral surface thereof.

In other words, the housing 8 has a portion, which surrounds a part where the first slit 31 of the valve element 7 exists and is higher than the external peripheral surface (external surface) 71 of the part where the first slit 31 exists, on the external peripheral side of the valve element 7 and in the vicinity of the first slit 31.

A thickness (wall thickness) of the housing 8 is preferably in the order of 0.2 to 10 mm and more preferably in the order of 0.5 to 5 mm.

In addition, a diameter of the opening 84 is preferably in the order of 0.1 to 30 mm and more preferably in the order of 2 to 10 mm.

Consequently, a human (living body), an object, or the like can be more surely prevented from touching the external peripheral surface 71 of the valve section 3 of the valve element 7 (external peripheral surface 71 in the vicinity of the first slit 31) by mistake, and adherence of bacteria or the like on the external peripheral surface 71 of the valve section 3 of the valve element 7 can be prevented more surely.

According to this mixing and injecting device 1, the same effect as the mixing and injecting device 1 of the aforementioned third embodiment is obtained.

Further, in this mixing and injecting device 1, as described above, the external peripheral surface 71 of the valve section 3 of the valve element 7 (external peripheral surface 71 in the vicinity of the first slit 31) can be cleaned easily and surely and, at the same time, peripheral equipment or the like can be prevented or inhibited from contacting the external peripheral surface 71 of the valve section 3 of the valve element 7 to contaminate the external peripheral surface 71 without damaging easiness of the cleaning work.

In addition, the number of components can be reduced and cost reduction can also be achieved compared with the case in which a lid or the like covering the valve section 3 of the valve member 7 is provided.

Next, an eighth embodiment of the mixing and injecting device of the present invention will be described.

Figure 13:
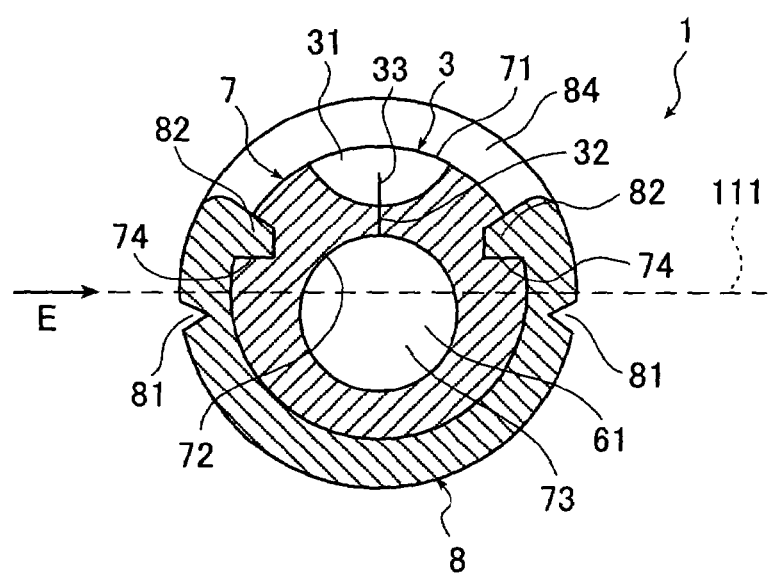
FIG. 13 is a transverse sectional view showing an eighth embodiment of the mixing and injecting device of the present invention.

FIG. 13 is a transverse sectional view showing an eighth embodiment of the mixing and injecting device of the present invention. Note that descriptions will be omitted regarding points common to the mixing and injecting device of this embodiment and the mixing and injecting device 1 of the aforementioned seventh embodiment, and main differences will be described.

As shown in the figure, in the external peripheral part of the valve element 7 of the mixing and injecting device 1, the pair of grooves 74 and 74 are formed along an axial direction of the valve element 7.

Further, the pair of ribs (protruded shape) 82 and 82 that can engage with the pair of grooves 74 and 74 are formed in a position in the internal peripheral part in the upper side in FIG. 13 of the housing 8 corresponding to the pair of grooves 74 and 74.

Consequently, rotation (displacement) or the like of the valve element 7 with respect to the housing 8 can be prevented.

Note that engaging means is constituted by the pair of grooves 74 and 74 and the pair of ribs 82 and 82.

According to this mixing and injecting device 1, the same effect as the mixing and injecting device 1 of the aforementioned seventh embodiment is obtained.

Further, since the grooves 74 are provided in the valve element 7 of this mixing and injecting device 1 and the ribs 82 that can engage with the grooves 74 are provided in the housing 8, rotation (displacement) or the like of the valve element 7 with respect to the housing 8 can be prevented.

In addition, in this mixing and injecting device 1, the valve element 7 can be mounted on the housing 8 easily compared with the case in which a valve element and a housing are adhered to each other with an adhesive. That is, the mixing and injecting device 1 can be manufactured (assembled) easily.

Note that, in the present invention, grooves may be provided in the housing 8 and ribs that can engage with the grooves may be provided in the valve element 7.

In addition, in the present invention, the engaging means is not limited to a combination of grooves and ribs, and examples of the engaging means include a combination of recessed portions and protruded portions, a combination of grooves and protruded portions, and the like in addition to the combination of grooves and ribs.

Next, a ninth embodiment of the mixing and injecting device of the present invention will be described.

Figure 14:
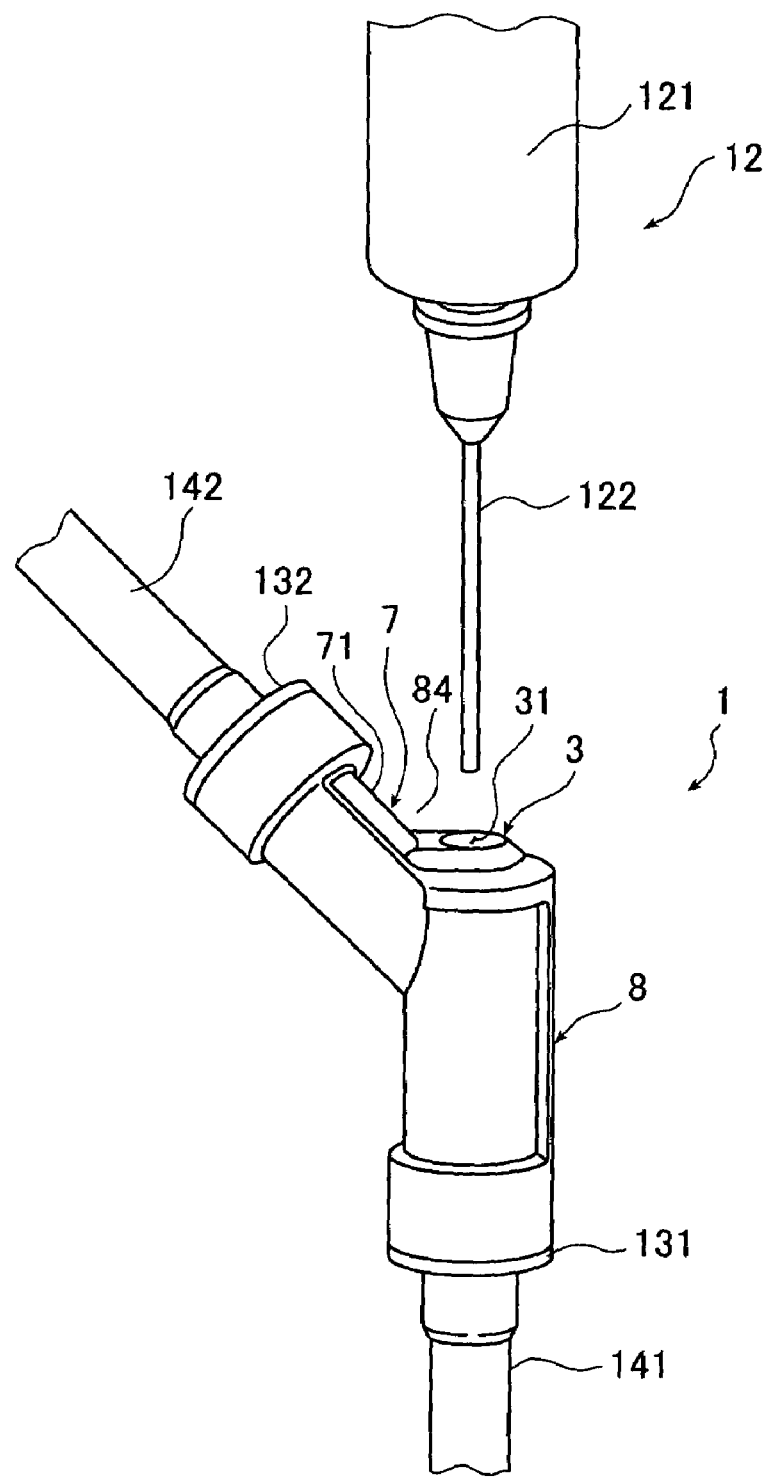
FIG. 14 is a perspective view showing a ninth embodiment of the mixing and injecting device of the present invention.
Figure 15:
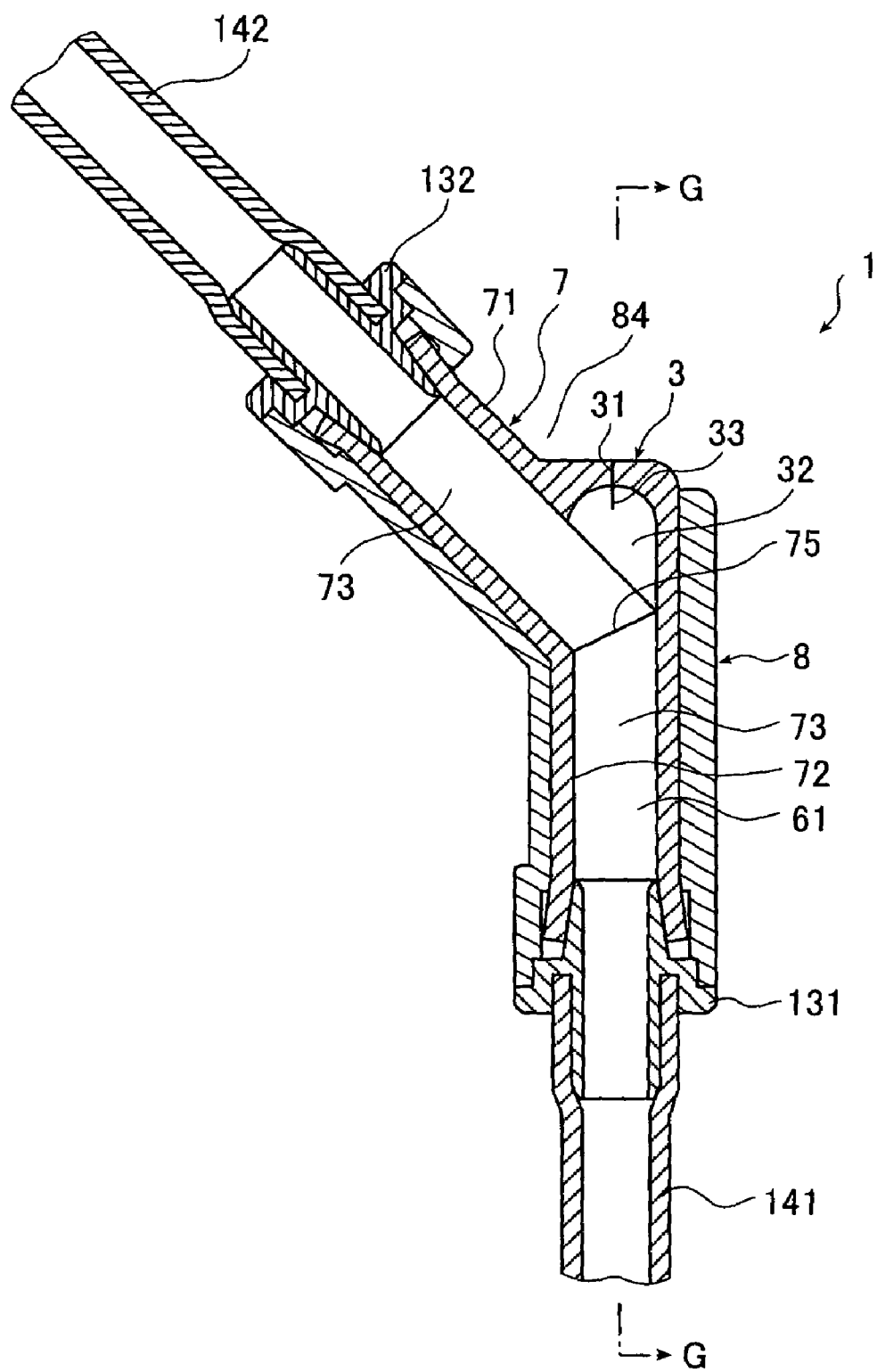
FIG. 15 is a longitudinal sectional view of the mixing and injecting device shown in FIG. 14.
Figure 16:
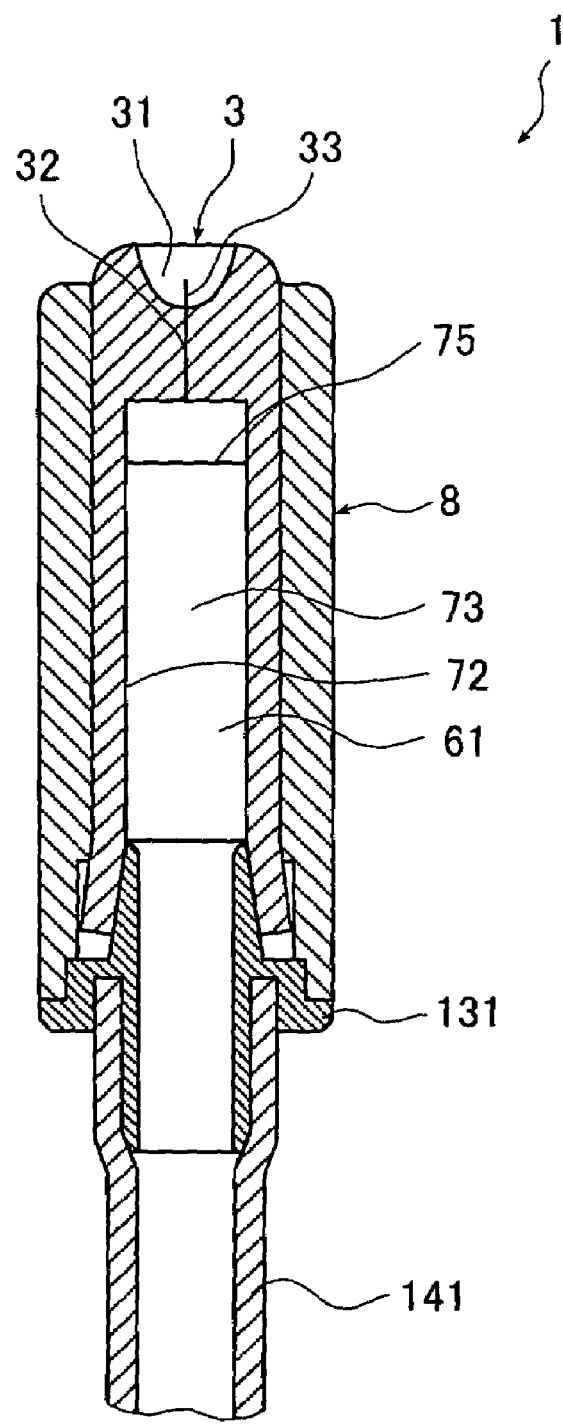
FIG. 16 is a sectional view (longitudinal sectional view) taken along line G—G in FIG. 15.

FIG. 14 is a perspective view showing the ninth embodiment of the mixing and injecting device of the present invention. FIG. 15 is a longitudinal sectional view of the mixing and injecting device shown in FIG. 14. FIG. 16 is a sectional view (longitudinal sectional view) along line G—G in FIG. 15. Note that descriptions will be omitted regarding points common to the mixing and injecting device of this embodiment and the mixing and injecting device 1 of the aforementioned seventh embodiment, and main differences will be described. In addition, for convenience of descriptions, an upper side is referred to as "upstream" and a lower side is referred to as "downstream" in FIG. 14, FIG. 15 and FIG. 16.

As shown in these figures, the valve element 7 of the mixing and injecting device 1 is bent such that the lumen 73 of the valve element 7 is formed in a V-shape, and the valve section 3 is provided in the bent portion 75.

In addition, the housing 8 is bent in a V-shape, and the opening 84 is formed in a part corresponding to the valve section 73 of the housing 8 and a part in the vicinity of the valve section 73. That is, the valve section 3 (first slit 31) of the valve element 7 is located in this opening 84, and the external peripheral surface 71 of the valve section 3 (the external peripheral surface 71 in the vicinity of the first slit 31) is exposed from the opening 84.

In addition, the vicinity of the second slit 32 of the valve element 7 is compressed in a lateral direction in FIG. 16 by the housing 8, whereby the inner surfaces of the second slit 32 are brought into press contact with each other.

In order to apply such a compressing force to the valve element 7 by the housing 8, for example, the cross section of the valve element 7 need only have a substantially ellipsoidal external shape with a direction of the first slit 31 as the longer diameter (major axis).

A tubular coupling member 131 is secured to an end on a downstream side of this housing 8 (lower side in FIG. 14 and FIG. 15). Further, an upstream side of a tube 141 fits in a downstream side of this coupling member 131.

In addition, a tubular coupling member 132 is secured to an end on an upstream side of this housing 8 (upper side in FIG. 14 and FIG. 15). Further, a downstream side of a tube 142 fits in an upstream side of this coupling member 132.

Note that a main part of the flow path 61 is constituted by the lumen 73 of the valve element 7, lumens of the coupling members 131 and 132, and lumens of the tubes 141 and 142.

As shown in FIG. 15, in this mixing and injecting device 1, a direction of the crossing section 33 of the first slit 31 and the second slit 32 and an axial direction of the lumen 73 on the downstream side (one end side) from the bent portion 75 of the valve element 7 coincide with each other, and the lumen 73 on the downstream side from the bent portion 75 is located on an extended line of the crossing section 33.

That is, the crossing section 33 and the central axis of the lumen 73 on the downstream side from the bent portion 75 coincide with each other.

Consequently, a relatively long hard pipe can be inserted into the flow path 61 (lumen 73) from the valve section 3 of the valve element 7.

In addition, the first slit 31 is provided in the external peripheral surface 71 of the valve element 7 so as to be perpendicular to a surface formed by an axis of the lumen 73 on the downstream side (one end side) from the bent portion 75 of the valve element 7 and an axis of the lumen 73 on the upstream side (the other end side) from the bent portion 75 of the valve element 7 (i.e., exactly the surface of FIG. 15). Moreover, the second slit 32 is provided in the internal peripheral surface 72 of the valve element 7, and the second slit 32 is on a surface identical with this surface.

In addition, the vicinity of the first slit 31 (external peripheral surface 71 in the valve section 3) in the external peripheral surface 71 of the valve element 7 is a flat surface or a recessed surface.

Note that, in this embodiment, the external peripheral surface 71 in the valve section 3 is a flat surface as shown in FIG. 14 and FIG. 15, and a perpendicular line of the external peripheral surface 71 and the axial direction of the lumen 73 on the downstream side from the bent portion 75 of the valve element 7 coincide with each other. That is, the perpendicular line and the direction of the crossing section 33 of the first slit 31 and the second slit 32 coincide with each other.

According to this mixing and injecting device 1, the same effect as the mixing and injecting device 1 of the aforementioned seventh embodiment is obtained.

Further, in this mixing and injecting device 1, a relatively long hard pipe can be inserted into the flow path 61 (lumen 73) from the valve section 3 of the valve element 7.

That is, as shown in FIG. 14, after sucking (absorbing) drug solution from a container containing the drug solution such as an ampoule or a vial by an injection instrument 12 constituted by connecting a blunt needle (tube body) 122 to a top of a syringe 121, the blunt needle 122 can be inserted from the valve section 3 to inject the drug solution without removing the blunt needle 122.

Consequently, the trouble of removing the blunt needle 122 from the syringe 121 is eliminated and, at the same time, the drug solution can be prevented from being contaminated when the blunt needle 122 is removed and a medicine such as an anticancer drug can be prevented from contacting medical personnel, and drug solution can be injected easily, promptly and surely.

Note that it is also possible to adjust the thickness (wall thickness) of the valve section 3 of the valve element 7 such that drug solution can be side-injected using a relatively short hard pipe (tube body).

In addition, it goes without saying that drug solution can be side-injected with a hard pipe with a length equivalent to the thickness (wall thickness) of the valve section 3 of the valve element 7.

Next, a tenth embodiment of the mixing and injecting device of the present invention will be described.

Figure 17:
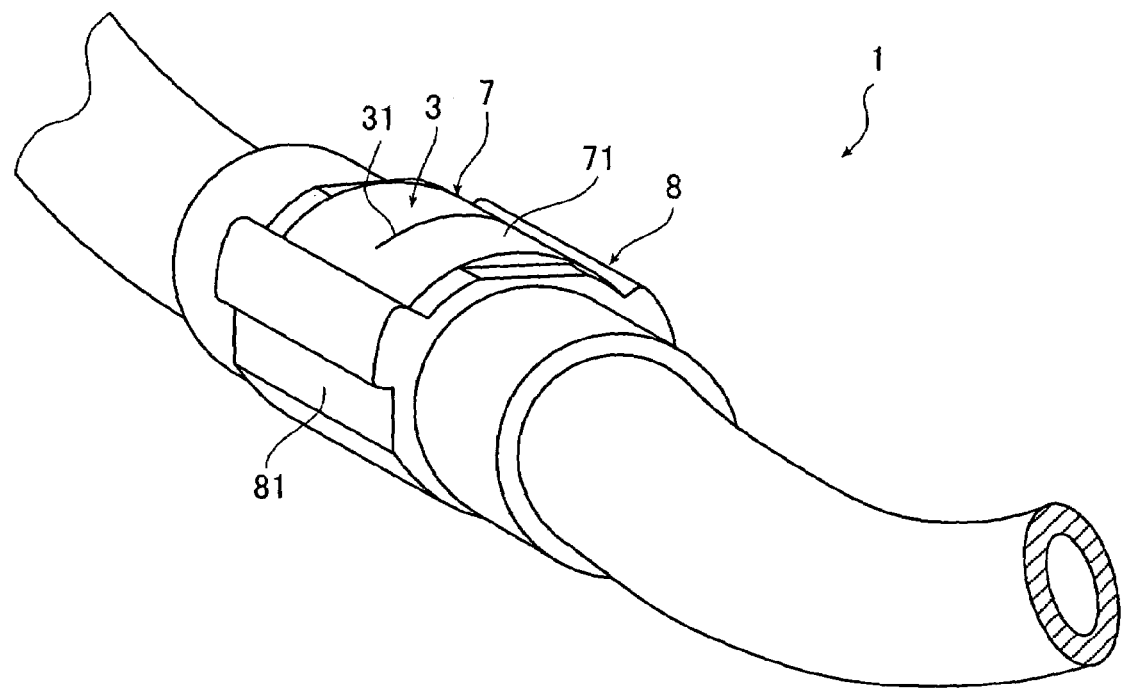
FIG. 17 is a perspective view showing a tenth embodiment of the mixing and injecting device of the present invention.
Figure 18:
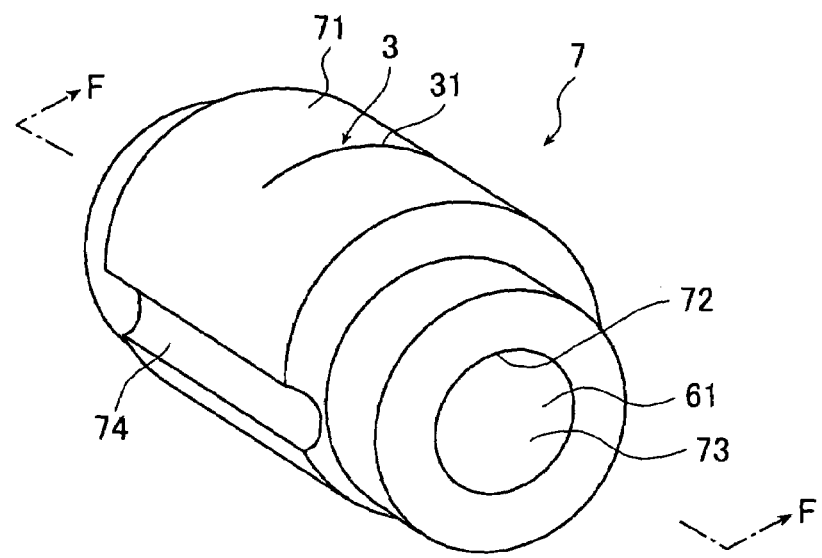
FIG. 18 is a perspective view showing an example of a structure of the valve element of the mixing and injecting device shown in FIG. 17.
Figure 19:
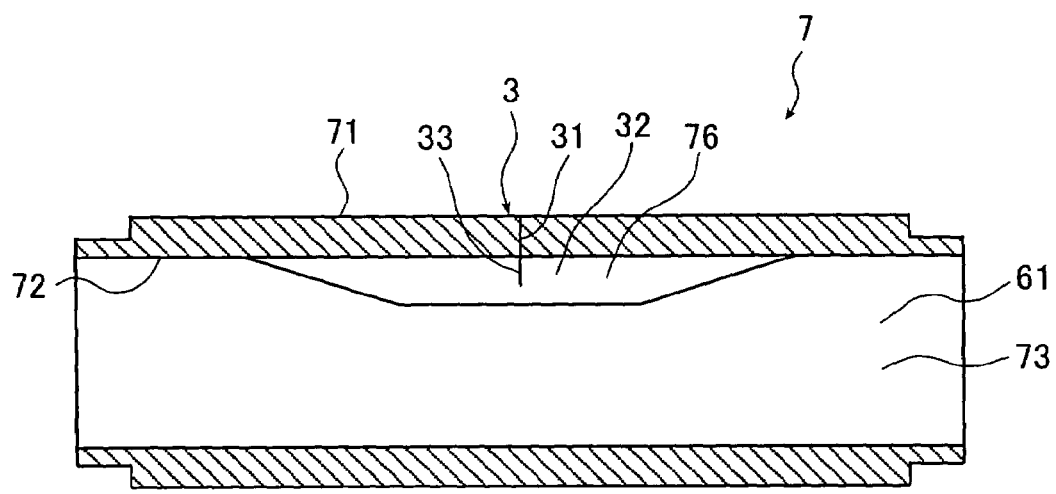
FIG. 19 is a sectional view (longitudinal sectional view) taken along line F—F in FIG. 18.

FIG. 17 is a perspective view showing the tenth embodiment of the mixing and injecting device of the present invention. FIG. 18 is a perspective view showing an example of a structure of a valve element of the mixing and injecting device shown in FIG. 17. FIG. 19 is a sectional view (longitudinal sectional view) along line F—F in FIG. 18. Note that descriptions will be omitted regarding points common to the mixing and injecting device of this embodiment and the mixing and injecting device 1 of the aforementioned fifth embodiment, and main differences will be described.

As shown in these figures, a protruded portion 76 is formed on an internal peripheral side of the valve section 3 of the valve element 7 of the mixing and injecting device 1 (in the vicinity of the crossing section 33).

In other words, a thickness of the valve element 7 is set such that a thickness of the valve section 3 (thickness in the vicinity of the crossing section 33), that is, a thickness of a part where the first slit 31 and the second slit 32 are located becomes largest in an axial direction and a peripheral direction of the valve element 7, respectively.

Note that it is preferable that the protruded portion 76 is relatively small and has a smooth shape. Consequently, liquid can flow more smoothly and surely.

According to this mixing and injecting device 1, the same effect as the mixing and injecting device 1 of the aforementioned fifth embodiment is obtained.

Next, a tube, a tube jointing device, a connection port manufacturing device, and a tube jointing system of the present invention will be described.

Figure 20:
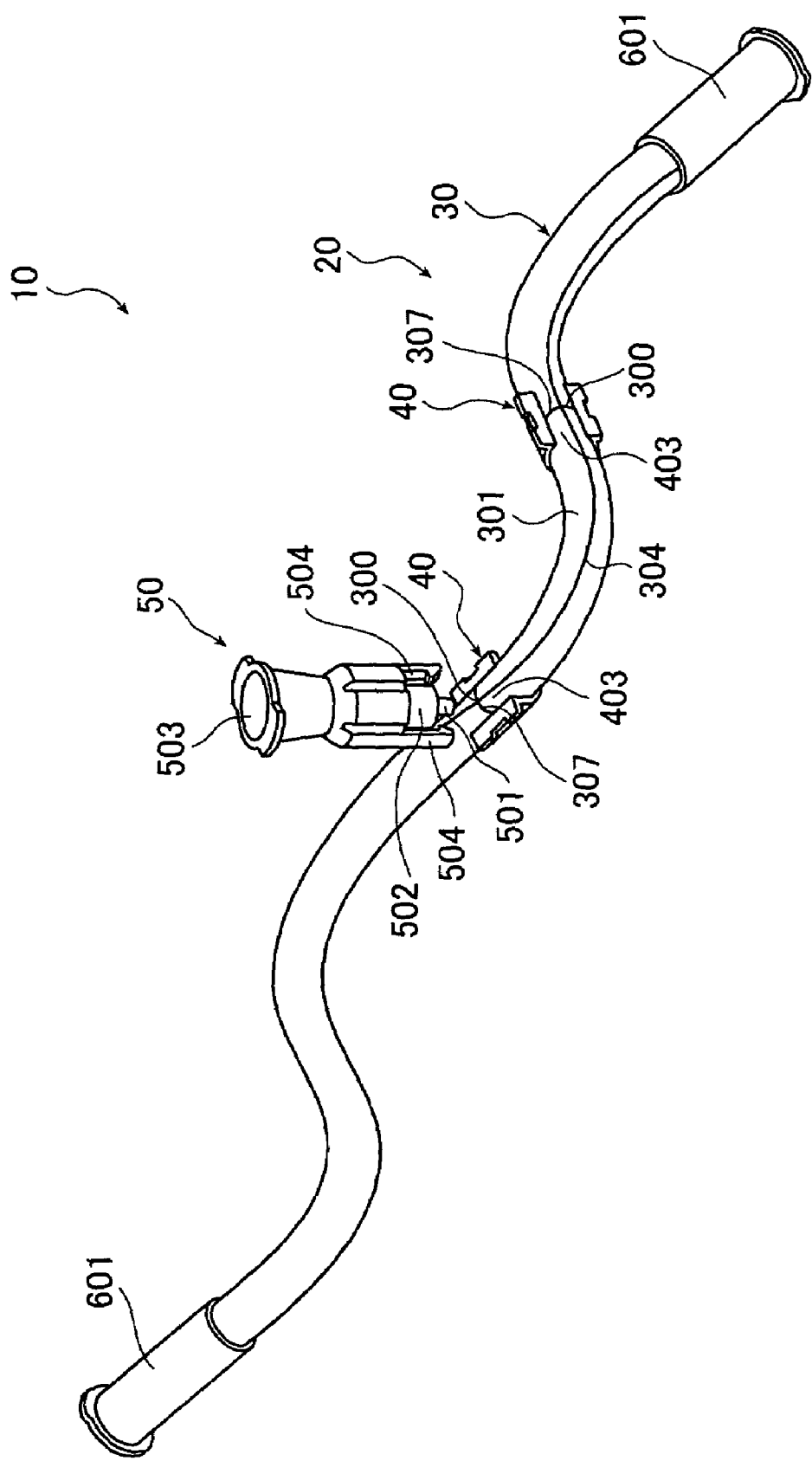
FIG. 20 is a perspective view showing an embodiment of a tube jointing system of the present invention.
Figure 21:
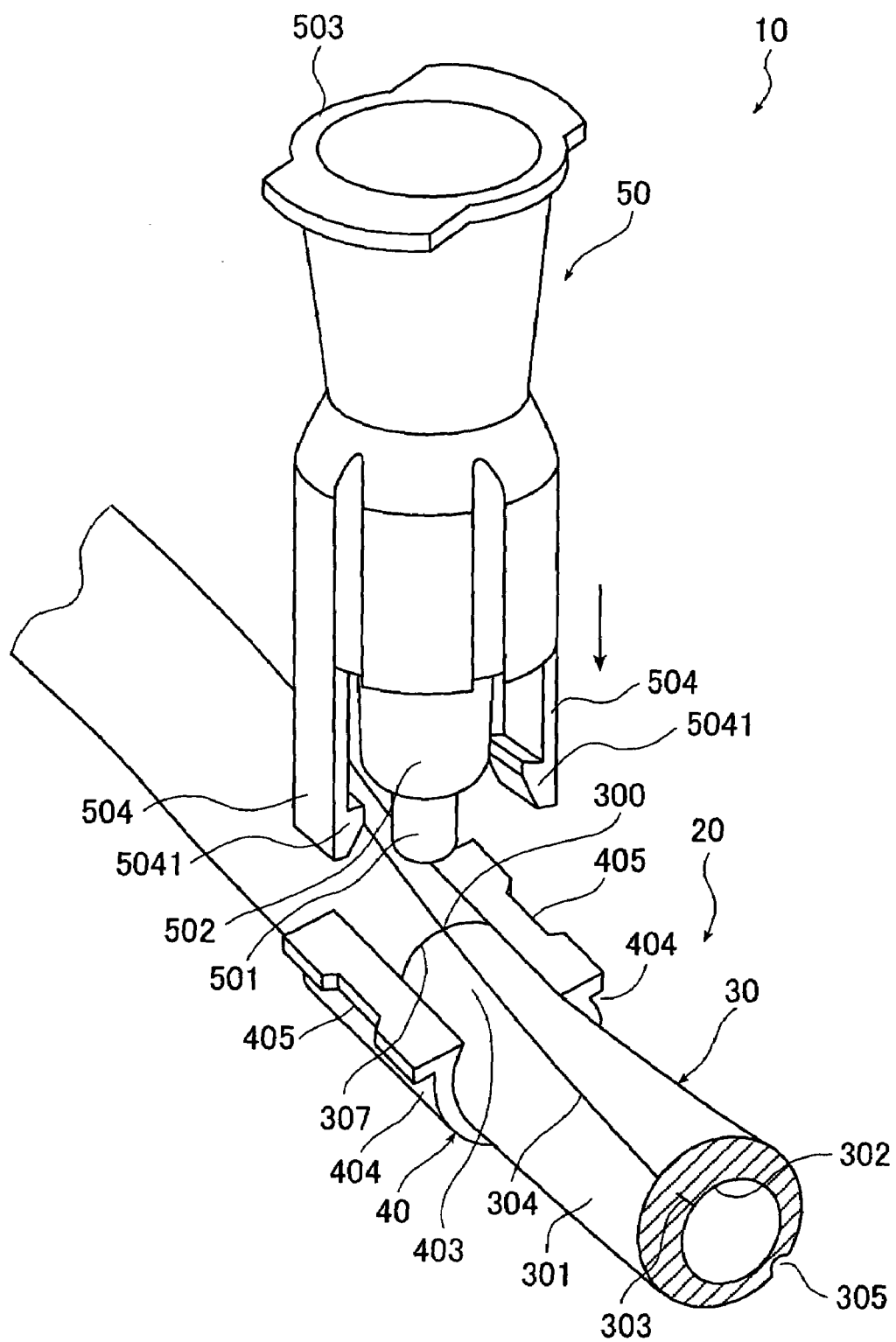
FIG. 21 is an enlarged perspective view showing a part of the tube jointing system shown in FIG. 20.
Figure 22:
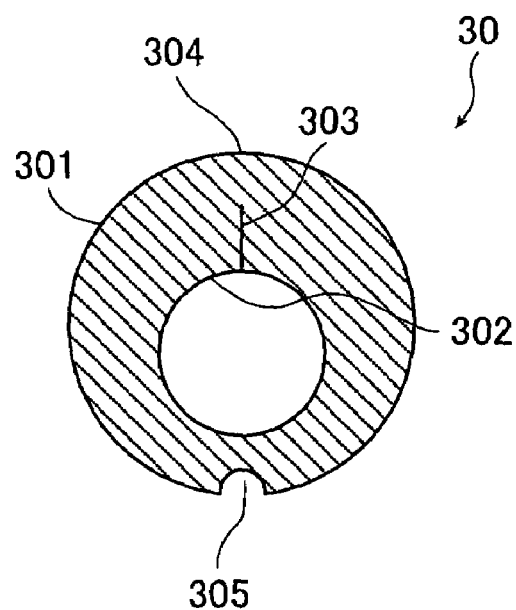
FIG. 22 is a transverse sectional view showing a tube shown in FIG. 20.
Figure 23:
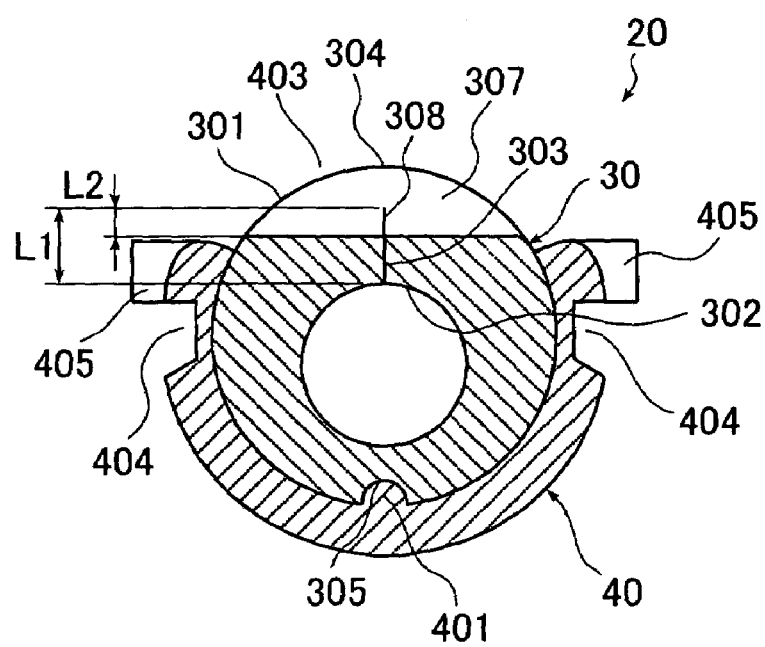
FIG. 23 is a transverse sectional view showing a first embodiment of a tube jointing device shown in FIG. 20.

FIG. 20 is a perspective view showing an embodiment of the tube jointing system of the present invention. FIG. 21 is an enlarged perspective view showing a part of the tube jointing system shown in FIG. 20. FIG. 22 is a transverse sectional view showing a tube shown in FIG. 20. FIG. 23 is a transverse sectional view showing a tube jointing device (first embodiment) shown in FIG. 20.

As shown in these figures, a tube jointing system 10 includes a tube jointing device 20 and a connector 50.

Further, the tube jointing device 20 includes a tube 30 and a hard housing 40 to be mounted on the tube 30, and the tube 30 is constituted by a cylindrical elastic body. Note that the housing 40 may be detachably attached to the tube 30 or may be constituted such that it cannot be removed from the tube 30 after being mounted thereon. However, the housing 40 is preferably constituted such that it cannot be removed from the tube 30 after being mounted thereon.

As shown in FIG. 21, an inner slit 303 in a closed state, which reaches an internal peripheral surface 302 and does not reach an external peripheral surface 301, is provided in the tube 30 as shown in FIG. 21. This inner slit 303 is formed along an axis of the tube 30.

Note that the inner slit 303 may be opened when the housing 40 is not mounted if, when the housing 40 is mounted, the inner slit 303 in the part of the housing 40 is closed (preferably, inner surfaces of the inner slit 303 are brought into press contact with each other).

A thickness of a part where this inner slit 303 of the tube 30 is provided is set thicker than the other parts.

In addition, this thickness of the part where the inner slit 303 of the tube 30 is provided is not specifically limited. However, a thickness of the tube 30, in particular, a thickness of the tube 30 in the part where the inner slit 303 is provided is preferably set to a thickness convenient for inserting a pipe according to conditions such as an external diameter (diameter) and a length of a hard pipe (tube body) 501 of the connector 50 to be inserted in a connection port 300 discussed later, a difference of pressures inside and outside the tube 30, and a press contact force of the inner surfaces of the inner slit 303, and more specifically, is preferably 0.1 times or more and more preferably in the order of 0.3 to 1 time as large as the external diameter (diameter) of the pipe 501. In addition, in order to cope with a relatively large difference of pressures inside and outside the tube 30, the thickness is preferably twice as large as the external diameter (diameter) of the pipe 501.

Note that the thickness of the tube 30 is not uniform in this embodiment but may be uniform in the present invention.

In addition, although a length (depth) L1 of the inner slit 303 is not specifically limited, the length is preferably in the order of 20 to 80% and more preferably in the order of 50 to 70% of a thickness of the tube 30 in a part where the inner slit 303 is provided.

Further, a guidepost (position indicating means) 304 is provided along the inner slit 303 on the external peripheral surface 301 of the tube 30. A position of the inner slit 303 can be grasped according to this guidepost 304.

Examples of the guidepost 304 include a continuous line as shown in the figure, a discontinuous line, a plurality of points or the like formed by printing or the like, a recessed portion like a groove, and the like.

In addition, a groove 305 is formed in an external peripheral part of the tube 30 along an axis thereof. This groove 305 is formed in a position turned by approximately 180° from the inner slit 303 around the axis of the tube 30.

Note that this groove 305 of the tube 30 may be a recessed portion.

In addition, connectors 601 that can be connected to not shown connection portions in a liquid tight state (air tight state) are secured to both ends of the tube 30.

Examples of a material constituting the tube 30 include elastic materials, for example, various kinds of rubbers such as natural rubber, isoprene rubber, butyl rubber, butadiene rubber, styrene-butadiene rubber, nitrile rubber, acrylic rubber, fluorine rubber, and silicone rubber, and various kinds of elastomers such as polyurethane, polyester, polyamide, olefin and styrene elastomers. One or more kinds of these materials can be mixed and used.

Note that, although the tube 30 is constituted by an elastic body in this embodiment, only a part of it has to be constituted by a flexible material in the present invention.

The housing 40 is constituted such that it can be mounted on the tube 30 by selecting an arbitrary position in an axial direction thereof.

A shape in a cross section of this housing 40 is substantially C-shaped. That is, an opened portion 403 for exposing a part of the external peripheral surface 301 of the tube 30 when the housing 40 is mounted on the tube 30 is formed in the housing 40.

In addition, a rib 401 for engaging with the groove 305 of the tube 30 when the housing 40 is mounted on the tube 30 is formed in the housing 40. This rib 401 is arranged such that the inner slit 303 is placed in the central part of the opened portion 403 when the housing 40 is mounted on the tube 30.

When the housing 40 is mounted on the tube 30, the rib 401 engages with the groove 305, whereby the housing 40 is prevented from moving (rotating) in a peripheral direction with respect to the tube 30.

Therefore, position regulating means for regulating a position in the peripheral direction of the housing 40 with respect to the tube 30 is constituted by the rib 401 and the groove 305.

Note that the rib 401 of this housing 40 may be a protruded portion.

When this housing 40 is mounted on the tube 30, the tube 30 is deformed (elastically deformed) by the housing 40 such that the inner surfaces of the inner slit 303 are brought into press contact with each other, and the tube 30 is held (nipped) by the housing 40. Consequently, the housing 40 is prevented from moving with respect to the tube 30 in an axial direction thereof.

Here, "deformation" refers to a state in which at least a part of the tube 30 changes to a different shape compared with a shape at the time when no external force is applied to the tube 30 (including the case in which a shape is similar and a dimension changes).

However, the housing 40 can be moved with respect to the tube 30 in an axial direction thereof by slightly opening the housing 40 toward the outside. In this case, the groove 305 of the tube 30 functions as a guide in moving the housing 40 in the axial direction.

In addition, a pair of grooves 404 and 404 that can engage with pawls 5041 and 5041 of a pair of elastic pieces 504 and 504 of the connector 50 discussed later are formed in the external peripheral part of the housing 40.

The grooves 404 extend in an axial direction of the housing 40 (axial direction of the tube 30 at the time when the housing 40 is mounted on the tube 30), respectively.

In addition, a pair of cutout portions 405 and 405 that can engage with the pair of elastic pieces 504 and 504 of the connector 50 discussed later are formed on an external peripheral side of an end on the upper side in FIG. 21 of the housing 40.

Examples of a material constituting this housing 40 include various kinds of resins such as polycarbonate, polysulphone, polyethylene, polypropylene, polystyrene, polyethylene terephthalate, polyethylene naphthalate, poly-acrylate, polyamide, hard polyvinyl chloride, acrylonitrile-butadiene-styrene copolymer (ABS resin), cyclic polyolefin, fluoroplastic, and poly-(4-methylpentene-1), various kinds of metal such as stainless steel, aluminum, and titanium, various kinds of ceramics such as alumina, and a composite of these materials.

In this tube jointing device 20, the connection port 300 is formed by forming an outer slit 307, which crosses with the inner slit 303 in the inside of the tube 30, reaches the external peripheral surface 301, and does not reach the internal peripheral surface 302, in the position of the opened portion 403 of the tube 30. Note that a method of forming the outer slit 307 will be described later.

In this embodiment, this outer slit 307 and the inner slit 303 cross with each other in a cross shape, that is, a crossing angle of the outer slit 307 and the inner slit 303 is 90°. However, this crossing angle is not limited to 90°.

In addition, as described above, the inner surfaces of the inner slit 303 of the connection portion 300 are brought into press contact with each other, and the outer slit 307 is closed.

Further, in this embodiment, a crossing section 38 where the outer slit 307 and the inner slit 303 cross with each other is linear.

A length L2 of this crossing section 38 of the outer slit 307 and the inner slit 303 is not specifically limited, but is preferably in the order of 20 to 50% and more preferably in the order of 30 to 40% of a thickness of the tube 30 of the part of the connection port 300.

The connector 50 includes the hard pipe (tube body) 501 on its tip side (lower side in FIG. 21) and includes a female luer 503 on its base end side (upper side in FIG. 21).

For example, a not-shown syringe or the like can be connected to this female luer 503.

Note that a not-shown tube may be connected to the base end side of the connector 50.

In addition, an expanded diameter portion 502 having an external diameter larger than the external diameter of the pipe 501 is provided on a base end side of the pipe 501 of the connector 50. When the connector 50 is connected to the connection port 300 of the tube 30, that is, when the pipe 501 of the connector 50 is inserted into the connection port 300 of the tube 30, this expanded diameter portion 502 abuts the external peripheral surface 301 of the tube 30, whereby an insertion depth of the pipe 501 into the tube 30 is regulated.

A length of the pipe 501 is preferably set longer than a thickness of the tube 30 in the part of the connection port 300 and to a degree that does not allow the tip of the pipe 501 to contact the internal peripheral surface 302 on the opposite side of the connection port 300 of the tube 30 when the connector 50 is connected to the connection port 300.

In addition, the opposed pair of elastic pieces 504 and 504 are formed in the external peripheral part of the connector 50. The elastic pieces 504 are vertically provided toward the axial direction of the connector 50, respectively, and the pawls 5041 projecting toward the pipe 501 side are formed in tip portions thereof, respectively.

Note that engaging means is constituted by the elastic pieces 504 of this connector 50 and the grooves 404 of the housing 40.

Examples of a material constituting this connector 50 include the same ones as those for the housing 40.

Next, actions of the tube jointing system 10 will be described.

First, a predetermined position in the axial direction of the tube 30 (position to which the connector 50 is to be connected) is selected, and the housing 40 is mounted on the position.

When the housing 40 is mounted on the tube 30, the rib 401 engages with the groove 305, the inner slit 303 is located in the central part of the opened portion 403 of the housing 40, and the housing 40 is prevented from moving (rotating) with respect to the tube 30 in a peripheral direction thereof. In addition, the tube 30 is held by the housing 40, whereby the housing 40 is prevented from moving with respect to the tube 30 in an axial direction thereof.

Subsequently, for example, the outer slit 307 is formed in a part located in the opened portion 403 of the tube 30 with a not-shown cutter (blade) or the like while confirming a position of the inner slit 303 according to the guidepost 304. Consequently, the connection port 300 is formed.

Subsequently, as shown in FIG. 21, the connector 50 is connected to the connection port 300 of the tube.

In this case, the connector 50 is grasped by fingers, and the pipe 501 of the connector 50 is located in the position of the connection port 300 and pushed into the connection port 300. Consequently, the pipe 501 is inserted into the tube 30 from the connection port 300, and at the same time, the elastic pieces 504 of the connector 50 move along the cutout portions 405 of the housing 40, respectively, and the pawls 5041 of the elastic pieces 504 engage with the grooves 404, respectively.

In this case, the pawls 5041 of the elastic pieces 504 engage with the grooves 404, respectively, whereby a position of the connector 50 with respect to the tube 30 and the housing 40 is regulated. That is, excessive insertion of the pipe 501 is prevented and, at the same time, disengagement of the pipe 501 after insertion is prevented.

In addition, the pawls 5041 of the elastic pieces 504 engage with the grooves 404, respectively, and the elastic pieces 504 engage with the cutout portions 405, respectively, whereby a posture of the connector 50 with respect to the housing 40 is maintained.

When the pipe 501 is inserted in the connection port 300, the inner surface of the crossing section 38 is in close adherence to the external peripheral surface of the pipe 501, and liquid tightness (air tightness) is maintained. In this state, for example, mixing and injection (side-injection) or sampling of liquid is performed.

Note that, in this tube jointing system 10, the connector 50 can be removed to connect another connector 50.

In addition, in this tube jointing system 10, the connection port 300 may be formed while the tube jointing system 10 is used or may be formed in advance before using the tube jointing system 10. Consequently, the tube jointing system 10 is used in extremely various ways.

Further, this tube jointing system 10 can be used as described below.

First, a plurality of positions where the connector 50 is connected to the tube 30 are determined, and the housing 40 is mounted in each of these positions.

Subsequently, the outer slit 307 is formed in a part of the tube 30 located in the opened portion 403 of each of the housing 40. Consequently, a plurality of connection ports 300 are formed.

Subsequently, the connector 50 is connected to a predetermined connection port 300 among the formed plurality of connection ports 300.

In addition, the connector 50 can be reconnected to another connection port 300 in the course of forming a flow path.

Further, connectors 50 can be connected to the plurality of connection ports 300, respectively.

As described above, according to this tube jointing system 10, the connection port 300 can easily be formed in an arbitrary position of the tube 30, and various types of flow path circuit formation can be performed.

In addition, a position of the inner slit 303 can be grasped according to the guidepost 304, whereby the connection port 300 can be formed surely.

In addition, a smooth flow path without a dead space or a step where liquid tends to hold up is formed. Consequently, liquid flows smoothly and surely. That is, turbulence is less likely to occur, and liquid can be prevented from holding up.

In addition, an operation at the time of connecting the connector 50 to the connection port 300 can be performed easily and safely (connection operability is high).

Further, since the inner surfaces of the inner slit 303 are in press contact with each other, liquid tightness is secured and leakage of liquid from the tube 30 can be prevented surely not only when nothing is inserted in (inserted through) the connection port 300 but also when, for example, the pipe 501 is inserted in the connection port 300, when a pipe of a different external diameter is inserted in the connection port 300, or when the pipe 501 is inserted into and pulled out from the connection port 300.

In addition, since the inner surfaces of the inner slit 303 are in press contact with each other, if the pipe 501 is inserted for a long period, the tube 30 is brought into a liquid tight state surely even after the pipe 501 is pulled out, and leakage of liquid from the tube 30 can be prevented surely. That is, durability is very high.

In addition, if a slight amount of liquid remains in the outer slit 307 or the inner slit 303, when the pipe 501 is pulled out, the outer slit 307 and the inner slit 303 close, respectively, and the liquid that has held up in the slits is completely discharged.

In addition, since the inner surfaces of the inner slit 303 are in press contact with each other, even if the width of the outer slit 307 is made relatively large, leakage of liquid from the tube 30 can be prevented.

Further, by making the width of the outer slit 307 relatively large, a frictional resistance at the time of inserting the pipe 501 and at the time of pulling it out can be made relatively small. Consequently, operations such as insertion and pulling out of the pipe 501 can be performed more easily.

In addition, even if the inner surfaces of the outer slit 307 or the inner slit 303 in a part other than a cross section 308 are not in contact with the inserted pipe 501 over the entire periphery thereof, leakage of liquid from the tube 30 can be prevented. Consequently, a deformation amount of the tube 30 (the outer slit 307 and the inner slit 303) at the time when the pipe 501 is inserted can be made relatively small. Consequently, if the pipe 501 is inserted for a long period, the tube 30 is brought into a liquid tight state surely even after the pipe 501 is pulled out, and leakage of liquid from the tube 30 can be prevented surely.

In addition, the tube jointing system 10 is simple in structure.

Note that, in the present invention, the housing 40 may be constituted such that it can be mounted in an arbitrary position in the peripheral direction of the tube 30 or may be constituted such that it can be mounted in an arbitrary position in the axial direction and the peripheral direction of the tube 30.

In addition, in the present invention, the housing 40 may be constituted such that it can move in the peripheral direction of the tube 30 or may be constituted such that it can move in the axial direction and the peripheral direction of the tube 30.

In addition, in the present invention, a not-shown tube connected to the base end side of the connector 50 may be constituted like, for example, the aforementioned tube 30. That is, the not-shown tube may be constituted such that a connection port can be formed in an arbitrary position of the not-shown tube connected to the base end side of the connector 50, and a not-shown connector can be connected to the formed connection port. Consequently, more various types of flow path circuit formation can be performed.

Further, in the present invention, the tube 30 may be branched in the middle. In this case, for example, a connection port can be selected to perform various types of mixing and injection, sampling or the like via a branching point (branching section).

Next, a second embodiment of the tube joining device of the present invention will be described. Note that descriptions will be omitted regarding points common to the tube jointing device of this embodiment and the tube jointing device 20 of the aforementioned first embodiment, and main differences will be described.

Figure 24:
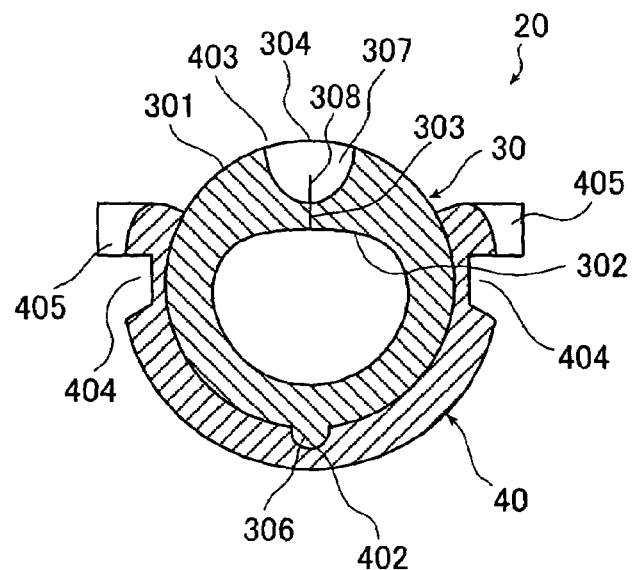
FIG. 24 is a transverse sectional view showing a second embodiment of the tube jointing device of the present invention.
Figure 25:
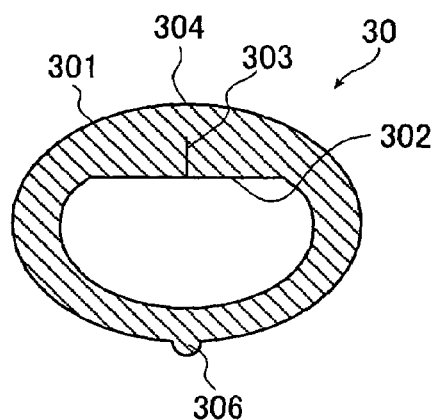
FIG. 25 is a transverse sectional view showing a tube shown in FIG. 24.

FIG. 24 is a transverse sectional view showing the second embodiment of the tube jointing device of the present invention. FIG. 25 is a transverse sectional view showing a tube shown in FIG. 24.

As shown in FIG. 25, an external shape in a cross section of the tube 30 of this tube jointing device 20 is substantially elliptical.

A rib 306 is formed in the external peripheral part of the tube 30 along an axis thereof. This rib 306 is formed in a position turned by approximately 180° from the inner slit 303 around the axis of the tube 30.

Note that the rib 306 of the tube 30 may be a protruded portion.

In addition, as shown in FIG. 24, a groove 402 with which the rib 306 of the tube 30 engages when the housing 40 is mounted on the tube 30 is formed in the housing 40. This groove 402 is arranged such that the inner slit 303 is located in the central part of the opened portion 403 when the housing 40 is mounted on the tube 30.

When the housing 40 is mounted on the tube 30, the rib 306 engages with the groove 402, whereby the housing 40 is prevented from moving (rotating) in a peripheral direction with respect to the tube 30.

Therefore, position regulating means for regulating a position in the peripheral direction of the housing 40 with respect to the tube 30 is constituted by the rib 306 and the groove 402.

Note that this groove 402 of the housing 40 may be a recessed portion.

According to this tube jointing device 20, the same effect as the tube jointing device 20 of the aforementioned first embodiment is obtained, for example, the connection port 300 can be formed easily in an arbitrary position.

Next, a third embodiment of the tube jointing device of the present invention will be described. Note that descriptions will be omitted regarding points common to the tube jointing device of this embodiment and the tube jointing device 20 of the aforementioned second embodiment, and main differences will be described.

Figure 26:
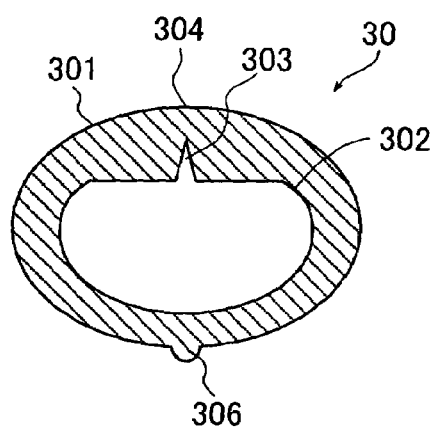
FIG. 26 is a transverse sectional view showing a tube in a third embodiment of the tube jointing device of the present invention.

FIG. 26 is a transverse sectional view showing a tube in the third embodiment of the tube jointing device of the present invention.

As shown in the figure, the inner slit 303 in an open state, which reaches the inner peripheral surface 302 and does not reach the external peripheral surface 301, is provided in the tube 30 of this tube jointing device 20. A shape in a cross section of this slit 303 is V-shaped.

According to this tube jointing device 20, the same effect as the tube jointing device 20 of the aforementioned second embodiment is obtained, for example, the connection port 300 can be formed easily in an arbitrary position.

Next, a fourth embodiment of the tube jointing device of the present invention will be described. Note that descriptions will be omitted regarding points common to the tube jointing device of this embodiment and the tube jointing device 20 of the aforementioned third embodiment, and main differences will be described.

Figure 27:
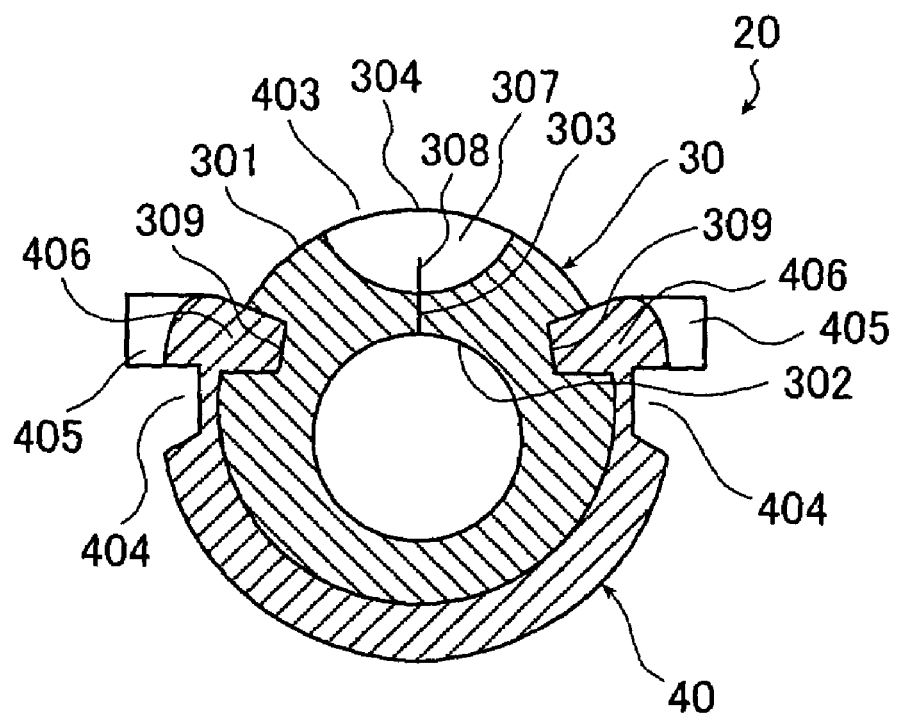
FIG. 27 is a transverse sectional view showing a fourth embodiment of the tube jointing device of the present invention.
Figure 28:
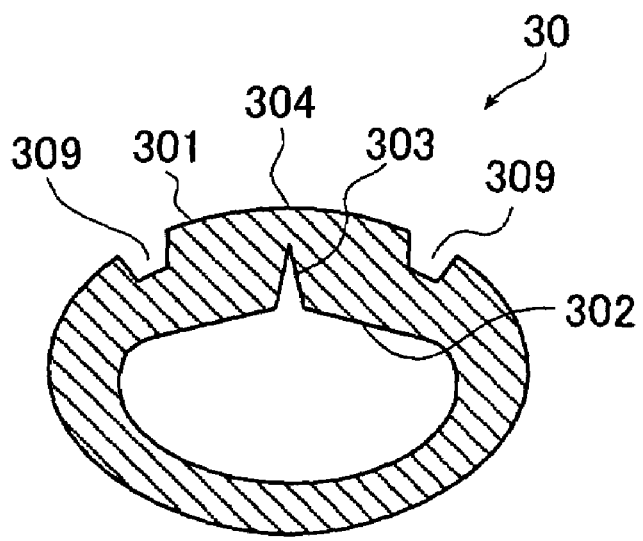
FIG. 28 is a transverse sectional view showing a tube shown in FIG. 27.

FIG. 27 is a transverse sectional view showing the fourth embodiment of the tube jointing device of the present invention. FIG. 28 is a transverse sectional view showing a tube shown in FIG. 27.

As shown in FIG. 28, a pair of grooves 309 and 309 are formed in the external peripheral part of the tube 30 of this tube jointing device 20 along an axis thereof. Each groove 309 is arranged symmetrically with respect to the inner slit 303 of the tube 30.

In addition, as shown in FIG. 27, a pair of ribs 406 and 406, which engage with the pair of grooves 309 and 309 of the tube 30 when the housing 40 is mounted on the tube 30, are formed on the inner peripheral side of the end on the upper side in FIG. 27 of the housing 40.

When the housing 40 is mounted on the tube 30, the ribs 406 engage with the corresponding groove 309, respectively, the housing 40 is prevented from moving (rotating) in a peripheral direction with respect to the tube 30, and the inner slit 303 is placed in the central part of the opened portion 403.

Therefore, position regulating means for regulating a position in the peripheral direction of the housing 40 with respect to the tube 30 is constituted by the ribs 406 and the grooves 309.

According to this tube jointing device 20, the same effect as the tube jointing device 20 of the aforementioned third embodiment is obtained, for example, the connection port 300 can be formed easily in an arbitrary position.

Next, another embodiment of the tube jointing system of the present invention will be described. Note that descriptions will be omitted regarding points common to the tube jointing system of this embodiment and the tube jointing system 10 of the aforementioned embodiment, and main differences will be described.

Figure 29:
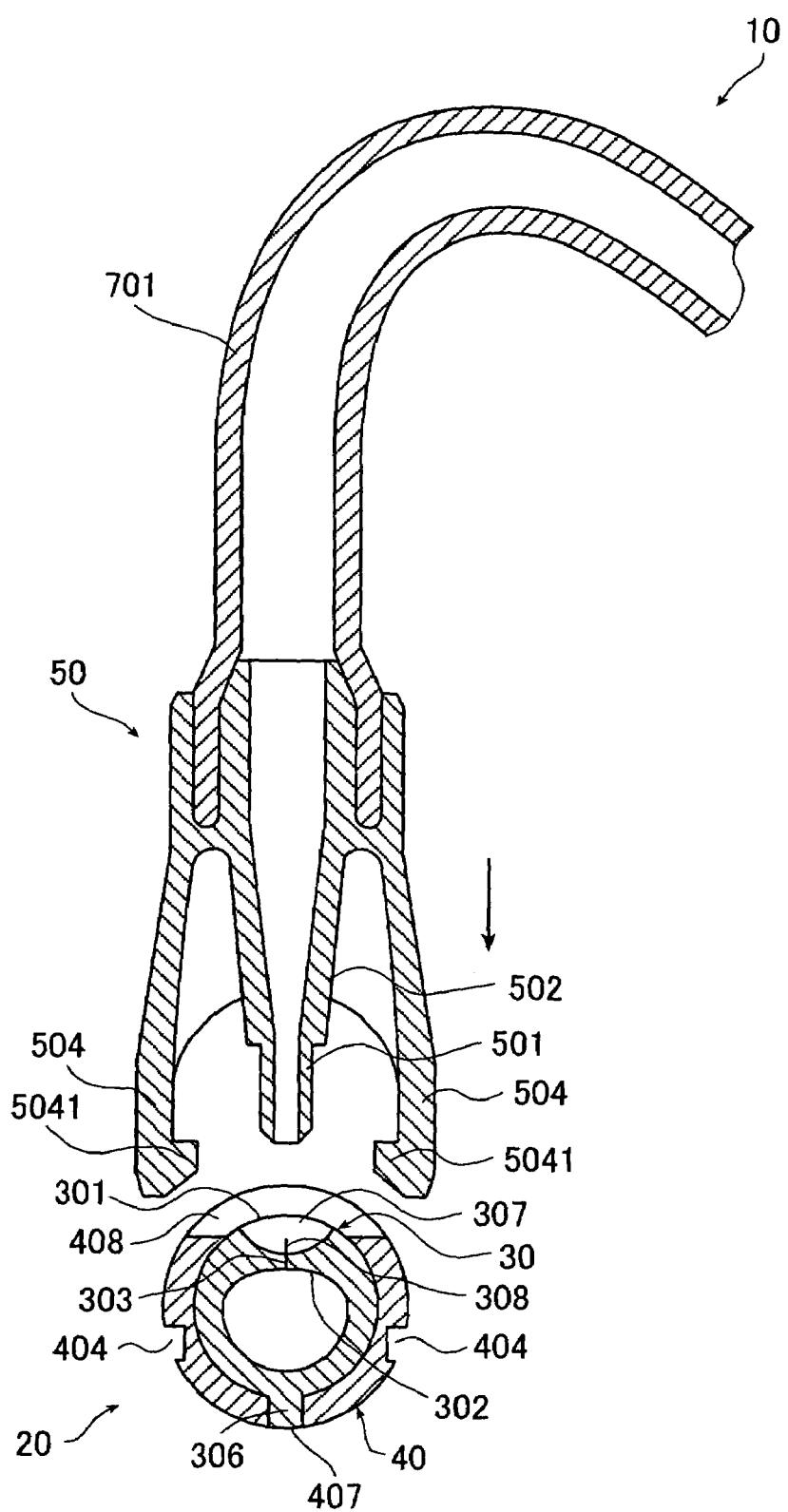
FIG. 29 is a sectional view showing another embodiment of the tube jointing system of the present invention.
Figure 30:
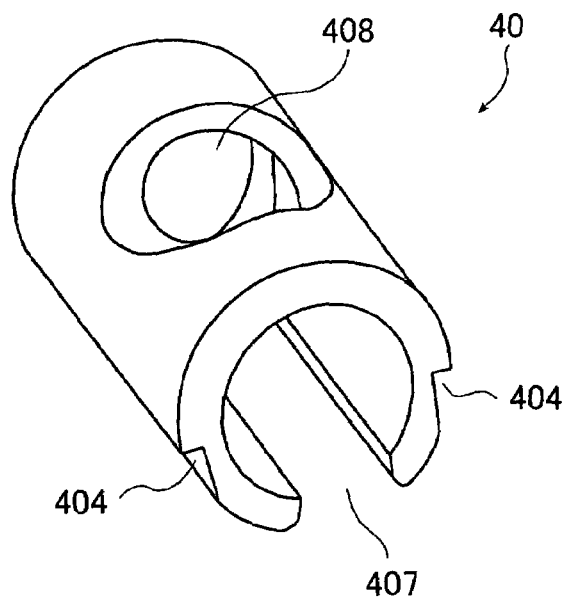
FIG. 30 is a perspective view showing a housing shown in FIG. 29.
Figure 31:
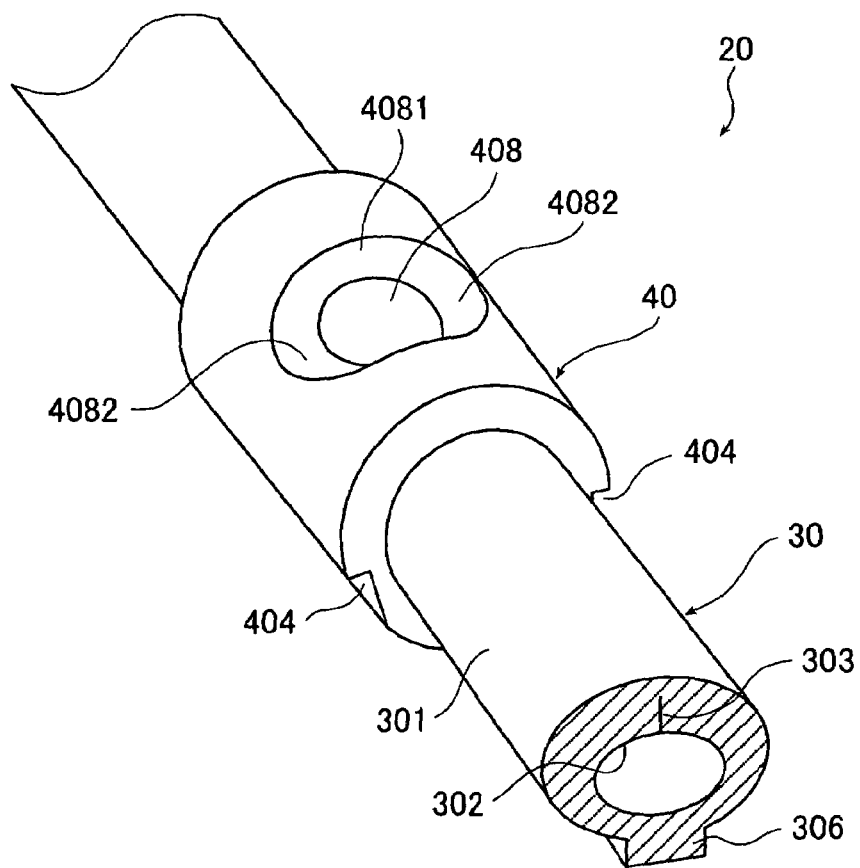
FIG. 31 is a transverse sectional view showing a fifth embodiment of a tube jointing device shown in FIG. 29.

FIG. 29 is a sectional view showing another embodiment of the tube jointing system of the present invention. FIG. 30 is a perspective view showing a housing shown in FIG. 29. FIG. 31 is a transverse sectional view showing a tube jointing device (fifth embodiment) shown in FIG. 29.

As shown in these figures, the rib 306 is formed in the external peripheral part of the tube 30 along an axis thereof. This rib 306 is formed in a position turned by approximately 180° from the inner slit 303 around the axis of the tube 30.

In addition, an opened portion 407, which engages with the rib 306 of the tube 30 when the housing 40 is mounted on the tube 30, is formed in the housing 40.

When the housing 40 is mounted on the tube 30, the rib 306 engages with the opened portion 407, and the housing 40 is prevented from moving (rotating) in a peripheral direction with respect to the tube 30.

Therefore, position regulating means for regulating a position in the peripheral direction of the housing 40 with respect to the tube 30 is constituted by the rib 306 and the opened portion 407.

In addition, an opening (opened portion) 408 is formed on the opposite side from the opened portion 407 of the external peripheral part of the housing 40. This opening 408 is formed in the central part in the axial direction of the housing 40. Note that, when the housing 40 is mounted on the tube 30, a part of the external peripheral surface 301 of the tube 30 is exposed from this opening 408.

In addition, as shown in FIG. 29, a tube 701 is connected to a base end side (upper side in FIG. 29) of the connector 50.

According to this tube jointing system 10, the same effect as the tube jointing system 10 of the aforementioned embodiment is obtained, for example, the connection port 300 can be formed easily in an arbitrary position.

The tube jointing system 10 of each embodiment described above further includes a cutter as a blade for forming the connection port 300 by forming the outer slit 307 in the tube 30. The tube jointing system 10 shown in FIG. 29 will be hereinafter described representatively.

Figure 32:
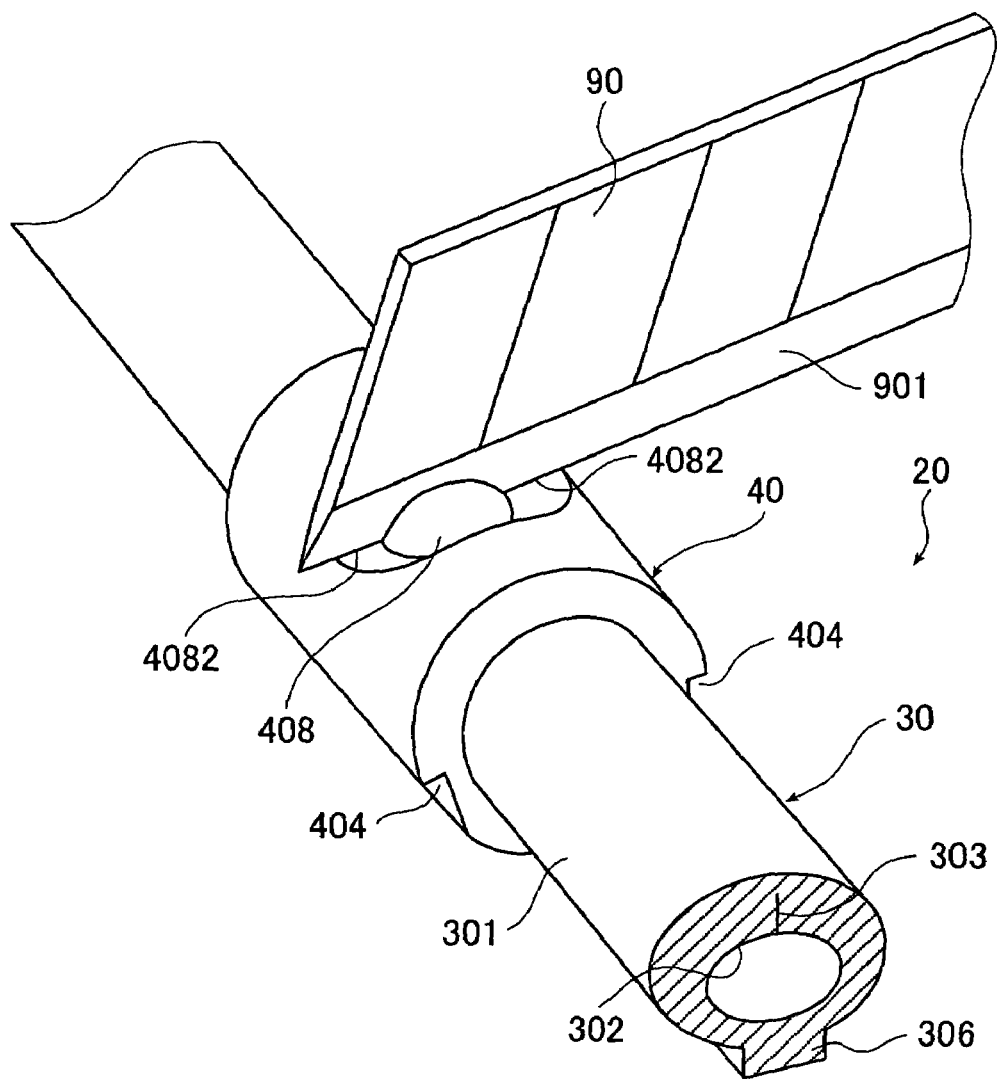
FIG. 32 is a perspective view showing a process of forming a connection port in the tube jointing device shown in FIG. 31 with a cutter.
Figure 33:
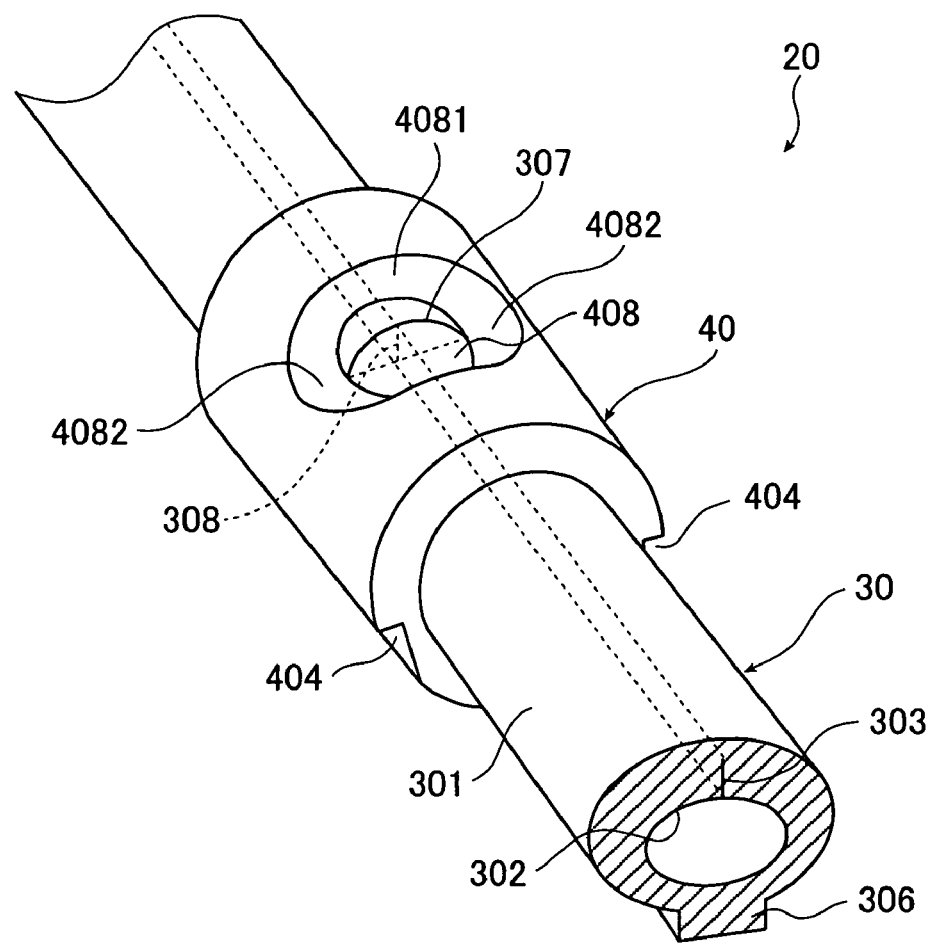
FIG. 33 is a perspective view showing a state in which the connection port is formed in the tube jointing device shown in FIG. 31.

FIG. 32 is a perspective view showing a process of forming a connection port in the tube jointing device shown in FIG. 31 with a cutter. FIG. 33 is a perspective view showing a state in which a connection port is formed in the tube jointing device shown in FIG. 31.

As shown in FIG. 32, the tube jointing system 10 further includes a cutter 90. A blade 901 having a linear blade surface is formed in this cutter 90.

In the case in which the connection port 300 is formed, as shown in FIG. 32, the cutter 90 is placed in the opening 408 of the housing 40, and the blade 901 of the cutter 90 is caused to abut a lowest part (bottom) 4082 of an edge portion 4081 facing the opening 408 of the housing 40. Then, the cutter 90 is moved along the bottom 4082 of the edge portion 4081. Consequently, as shown in FIG. 33, the outer slit 307 is formed in the tube 30. That is, the connection port 300 is formed.

In this case, a position and a direction of the blade 901 of the cutter 90, that is, a position and a direction of the outer slit 307 are regulated by the bottom 4082 of the edge portion 4081.

In addition, a depth of the outer slit 307 is regulated by the bottom 4082 of the edge portion 4081.

Consequently, the outer slit 307 can be formed easily and accurately.

Next, another embodiment of the tube jointing system of the present invention will be described. Note that descriptions will be omitted regarding points common to the tube jointing system of this embodiment and the tube jointing system 10 of the aforementioned each embodiment, and main differences will be described.

Figure 34:
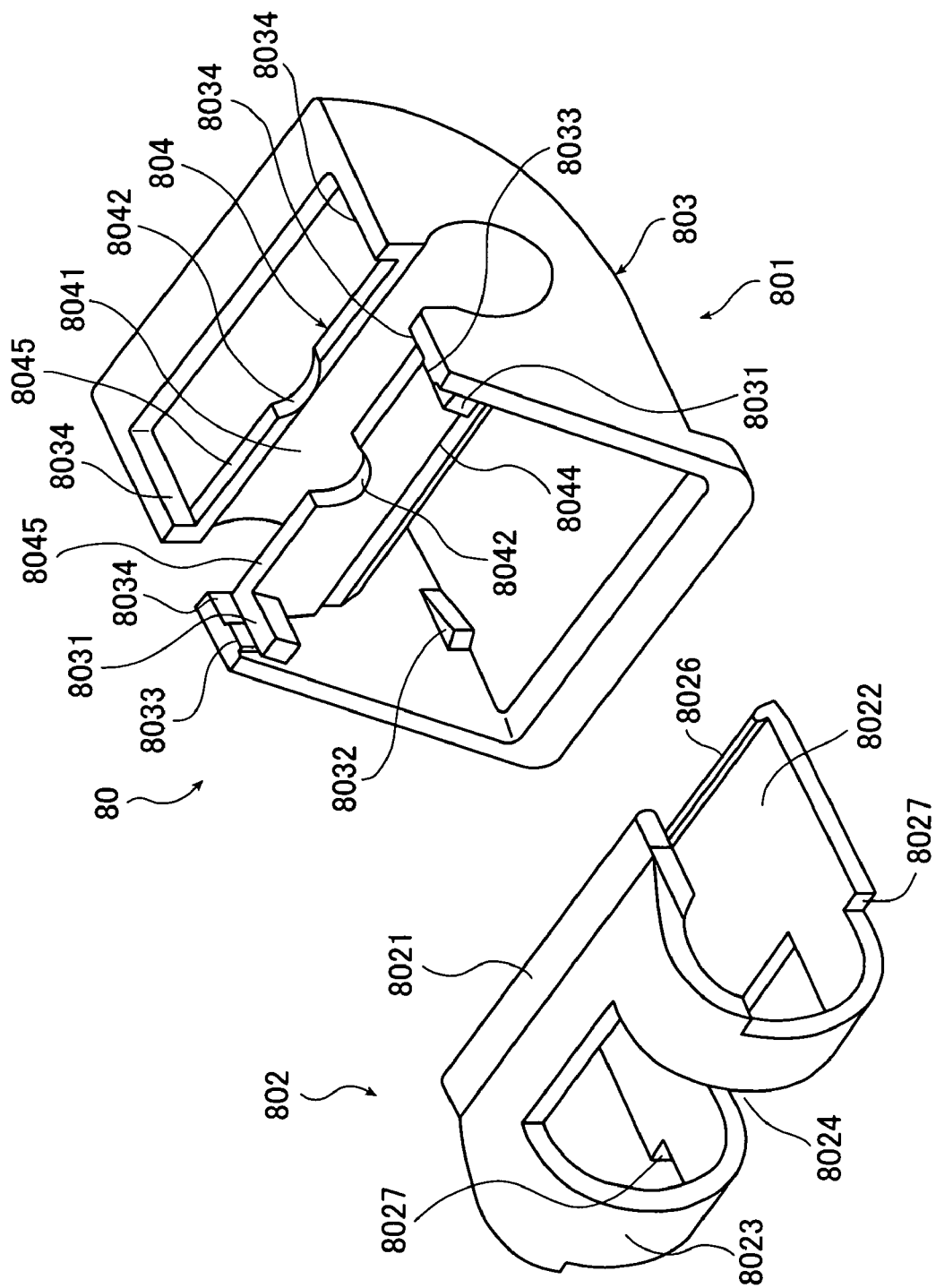
FIG. 34 is a perspective view showing an embodiment of a connection port manufacturing device in another embodiment of the tube jointing system of the present invention, which is in a state in which a cutter unit is removed.
Figure 35:
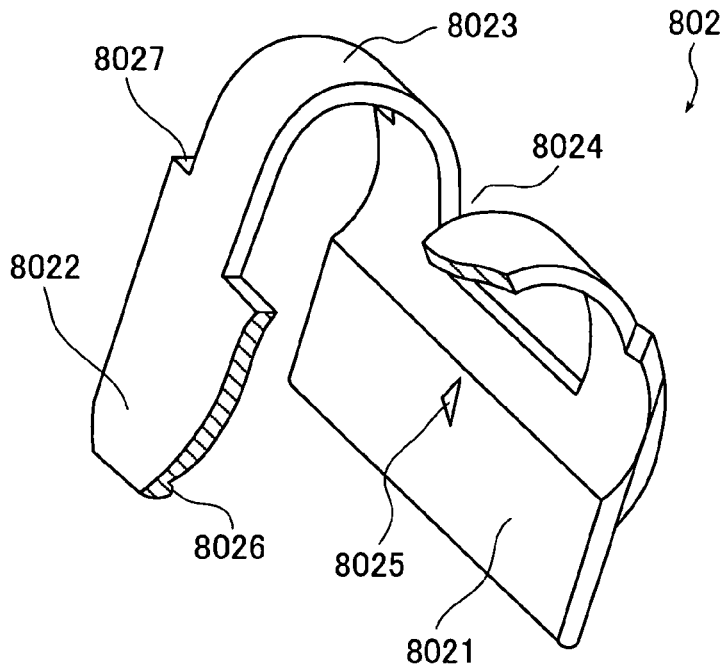
FIG. 35 is a perspective view showing the cutter unit of the connection port manufacturing device shown in FIG. 34, which is in a state in which a part of it is cut out.
Figure 36:
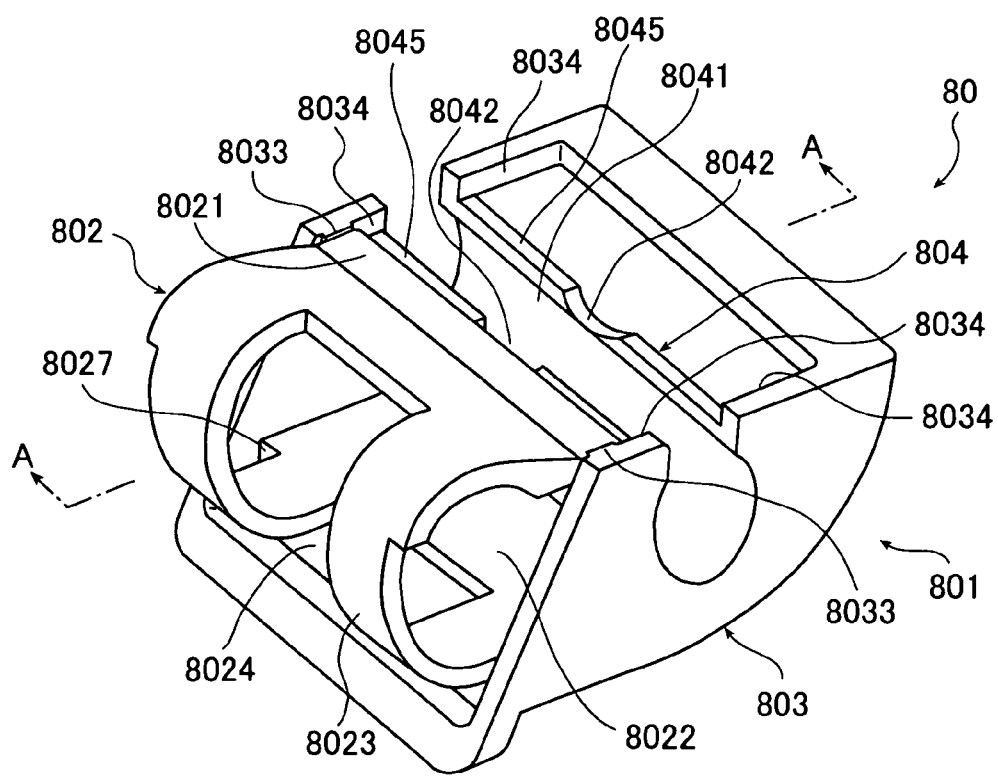
FIG. 36 is a perspective view showing the connection port manufacturing device shown in FIG. 34, which is in a state in which the cutter unit is mounted.
Figure 37:
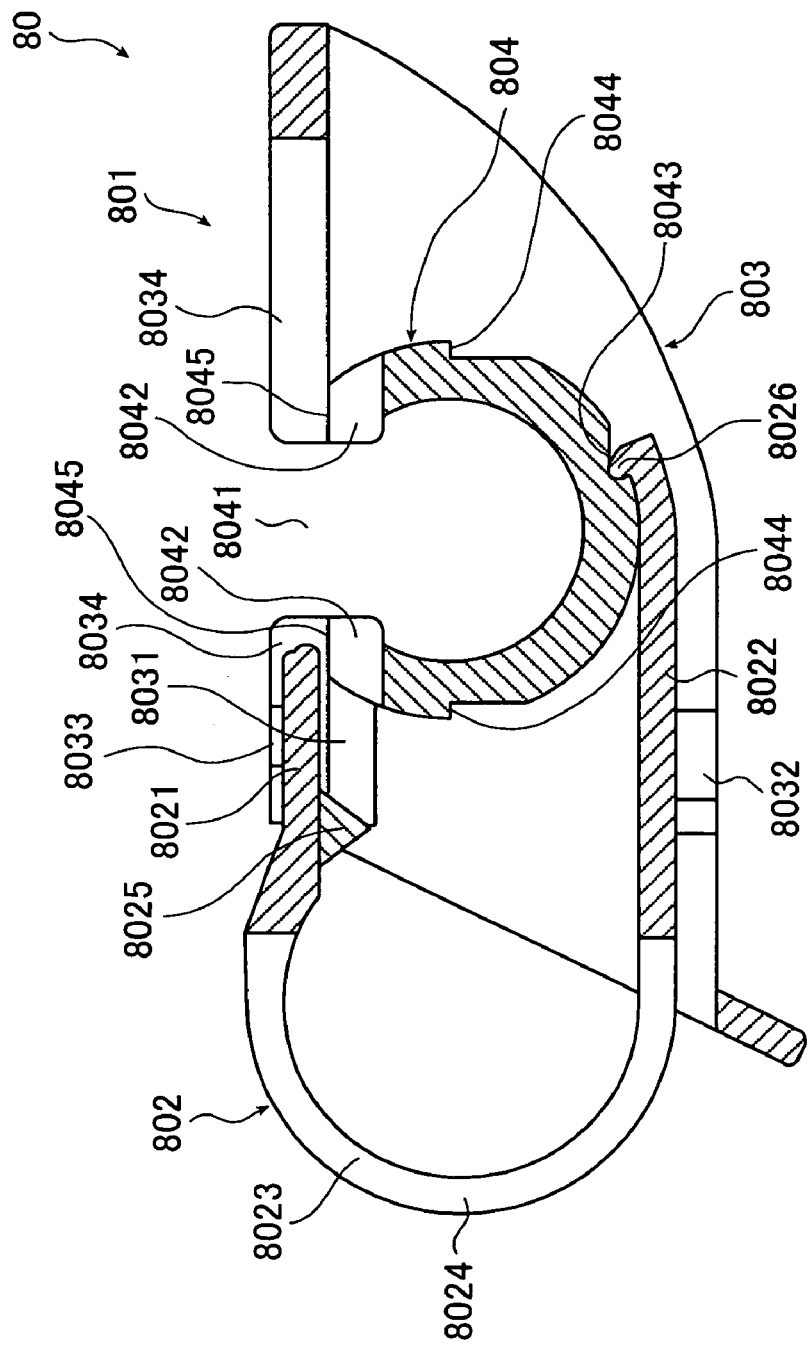
FIG. 37 is a sectional view taken along line A—A in FIG. 36.

FIG. 34 is a perspective view showing an embodiment of a connection port manufacturing device in another embodiment of the tube jointing system of the present invention, which is in a state in which a cutter unit is removed. FIG. 35 is a perspective view showing a cutter unit of the connection port manufacturing device shown in FIG. 34, which is in a state in which a part of the cutter unit is cut out. FIG. 36 is a perspective view showing a connection port manufacturing device shown in FIG. 34, which is in a state in which the cutter unit is mounted. FIG. 37 is a sectional view taken along line A-A in FIG. 36.

As shown in these figures, the tube jointing system 10 includes a connection port manufacturing device 80, and the not-shown tube 30 and connector 50.

The connection port manufacturing device 80 is constituted by a connection port manufacturing device main body 801 for detachably holding the tube 30 and a cutter unit 802 that is set such that it can be displaced with respect to the connection port manufacturing device main body 801.

The cutter unit 802 is constituted by a plate-like member, and an overall shape of the cutter unit 802 is substantially U-shaped. That is, the cutter unit 802 is constituted by a pair of flat portions 8021 and 8022 opposedly arranged substantially in parallel with each other and a curved portion 8023 connected to the left side in FIG. 34 of the flat portions 8021 and 8022.

An opening 8024 is formed in a central part of the curved portion 8023 of the cutter unit 802.

In addition, a substantially triangular blade 8025 is fixed on the side opposed to the flat portion 8022 of the flat portion 8021 of the cutter unit 802.

A direction of the blade 8025 is set so as to coincide with a moving direction of the flat portion 8021 at the time when the outer slit 307 is formed in the tube 30.

In addition, the blade 8025 is arranged substantially in the middle of a direction perpendicular to the moving direction of the flat portion 8021.

In addition, a rib 8026 is formed in a tip portion on the side opposed to the flat portion 8021 of the flat portion 8022 of the cutter unit 802.

Further, step portions 8027 are formed in both ends in a direction perpendicular to the moving direction of the flat portion 8021 of the curved portion 8023 of the cutter unit 802, respectively.

The connection port manufacturing device main body 801 includes a base 803 and a tube holding section 804 that is provided in this base 803 and detachably holds the tube 30.

The tube holding section 804 also serves as the aforementioned housing 40 and a shape in its cross section is substantially C-shaped. That is, an opened portion 8041, which exposes a part of the external peripheral surface 301 of the tube 30 when the tube 30 is mounted on the tube holding section 804, is formed on the upper side in FIG. 34 of the tube holding section 804.

In addition, a pair of grooves 8042 and 8042 are formed on the upper side in FIG. 34 of the tube holding section 804 and in a part where the blade 8025 of the cutter unit 802 passes. A depth of the groove 8042 is set larger than a height of the blade 8025 of the cutter unit 802.

Further, a groove 8043 that can engage with the rib 8026 of the cutter unit 802 is formed in the external peripheral part of the tube holding section 804.

This groove 8043 extends in an axial direction of the tube holding section 804 (axial direction of the tube 30 at the time when the tube 30 is mounted on the tube holding section 804).

Further, a pair of grooves 8044 and 8044 that can engage with the pawls 5041 and 5041 of the pair of elastic pieces 504 and 504 of the connector 50 is formed in the external peripheral part of the tube holding section 804.

The grooves 8044 extend in the axial direction of the tube holding section 804 (axial direction of the tube 30 at the time when the tube 30 is mounted on the tube holding section 804), respectively.

Note that engaging means is constituted by the elastic pieces 504 of the aforementioned connector 50 and the grooves 8044.

When the tube 30 is mounted on the tube holding section 804 of the connection port manufacturing device main body 801, the tube 30 is deformed (elastically deformed) by the tube holding section 804 such that the inner surfaces of the inner slit 303 are brought into press contact with each other, and the tube 30 is held (nipped) by the tube holding section 804. Consequently, the tube 30 is prevented from moving with respect to the tube holding section 804 in an axial direction and a peripheral direction thereof.

However, the tube 30 can be moved with respect to the tube holding section 804 in the axial direction and the peripheral direction thereof by slightly opening the tube holding section 804 toward the outside.

In addition, in the base 803, a pair of projections 8031 and 8031, a pair of projections 8033 and 8033, and a pair of projections 8032 and 8032 are provided, which abut a surface on the lower side in FIG. 37 of the flat portion 8021 of the cutter unit 802, a surface on the upper side in FIG. 37 of the flat portion 8021, and a surface on the lower side in FIG. 37 of the flat portion 8022, respectively, when the cutter unit 802 is mounted on this connection port manufacturing device main body 801. Note that the projections 8031 and 8033 are arranged on the upper side in FIG. 37 of the base 803, and the projections 8032 are arranged on the lower side in FIG. 37 of the base 803.

Examples of a material constituting this connection port manufacturing device 80 are the same as those for the housing 40.

Since the tube 30 and the connector 50 are the same as those in the aforementioned each embodiment, descriptions on them will be omitted.

Note that, in the present invention, a protruded portion may be provided in one of the tube 30 and the tube holding section 804, and a recessed portion engaging with the protruded portion may be provided in the other.

Further, in the present invention, the tube holding section 804 may be constituted in the same manner as the housing 40 in the aforementioned each embodiment.

Next, actions of the tube jointing system 10 will be described.

Figure 38:
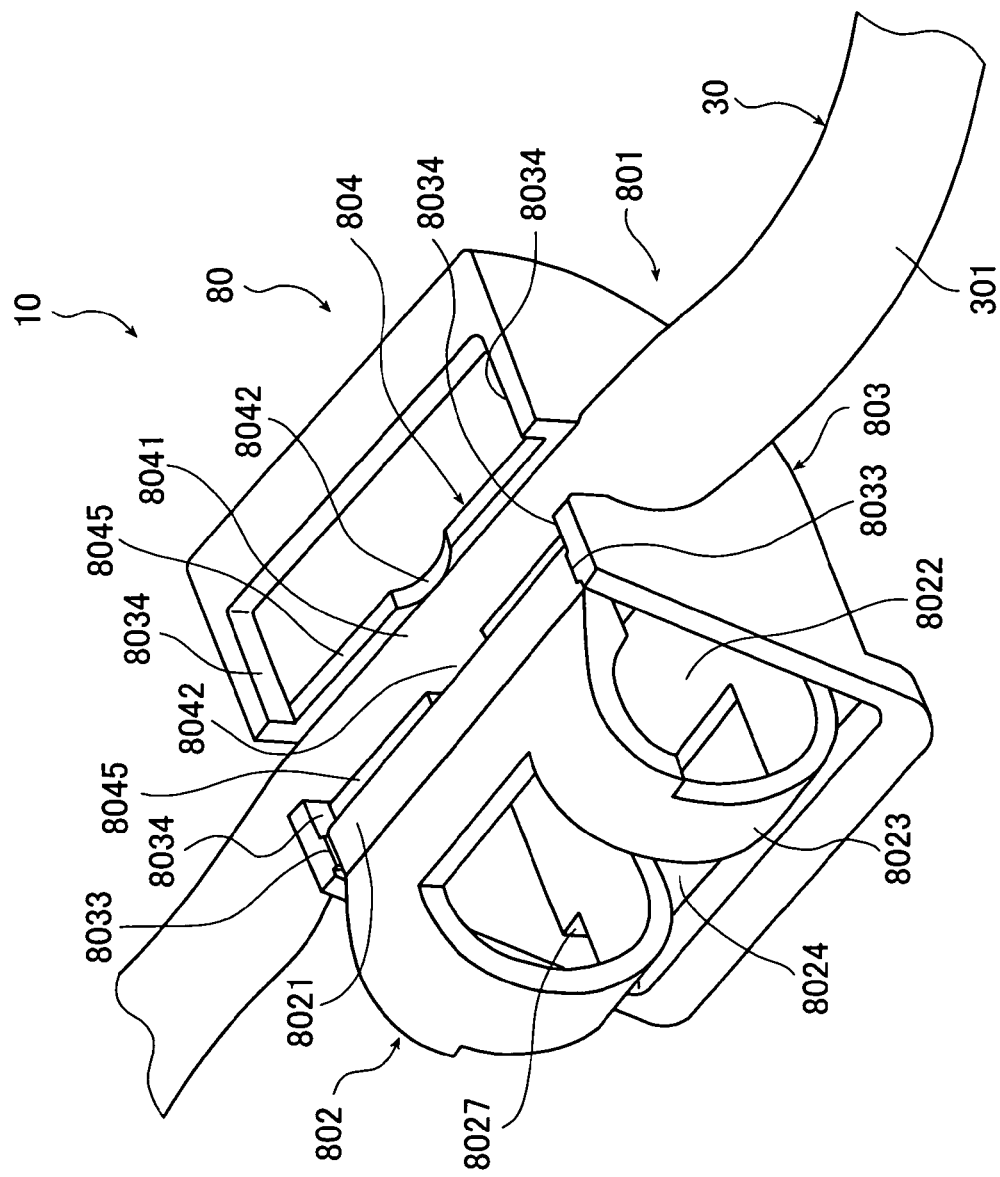
FIG. 38 is a perspective view for explaining an action of the tube jointing system shown in FIG. 34.
Figure 39:
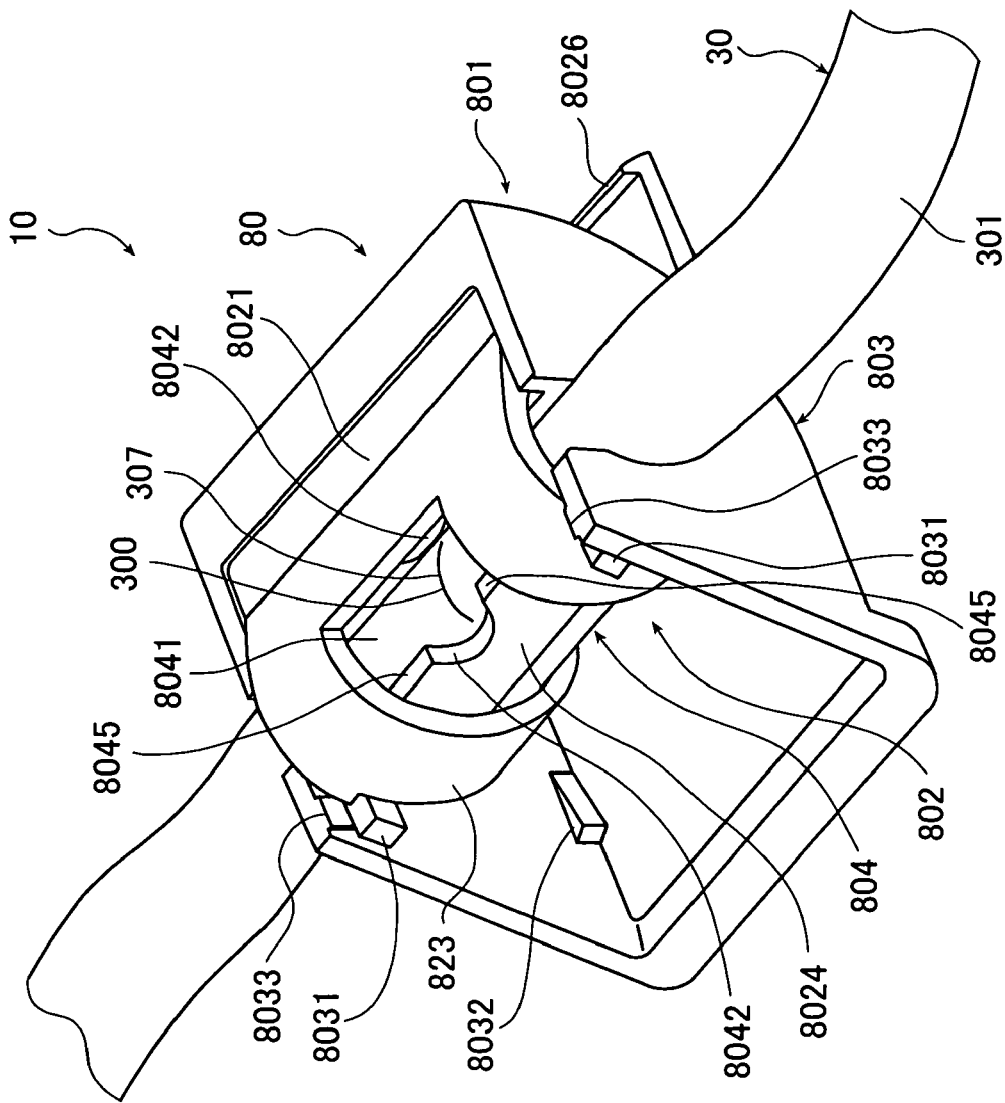
FIG. 39 is a perspective view for explaining an action of the tube jointing system shown in FIG. 34.
Figure 40:
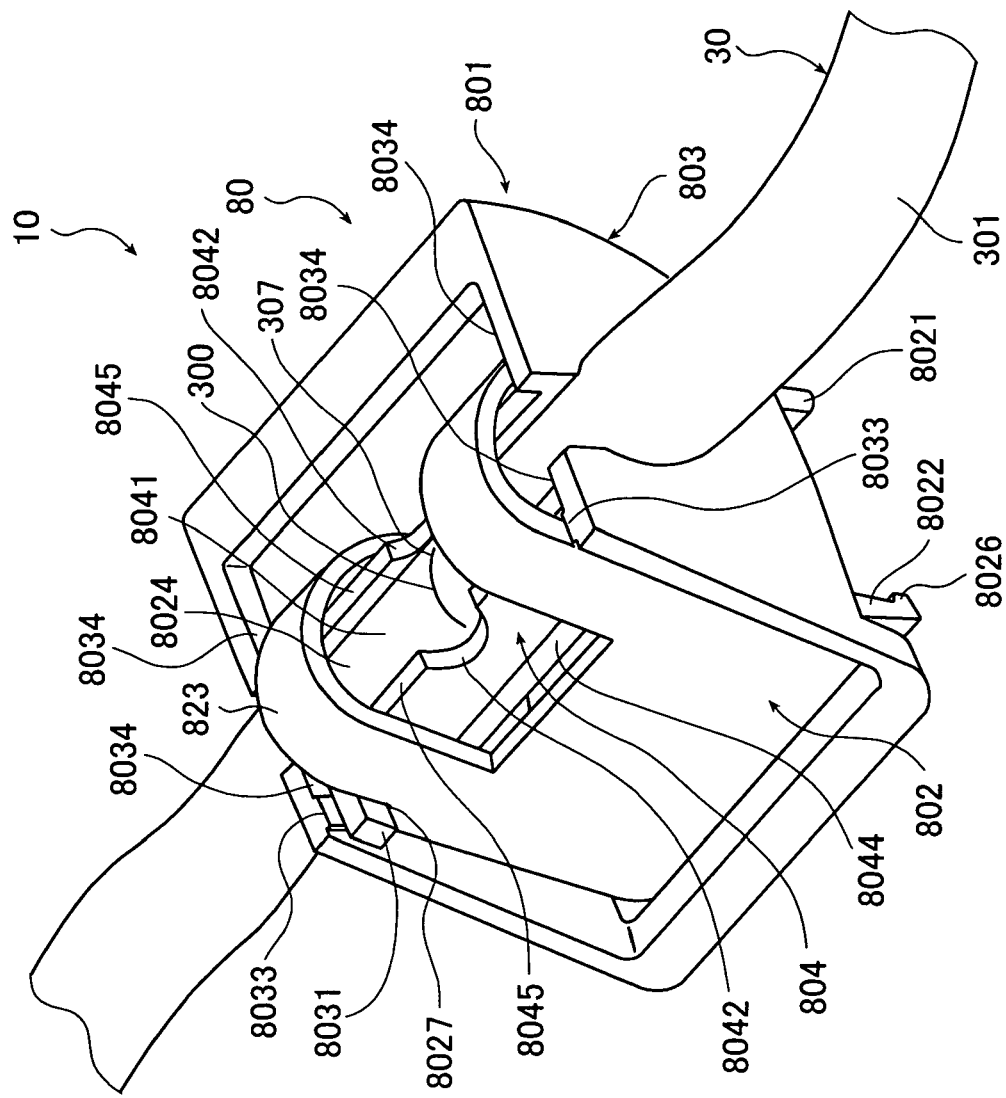
FIG. 40 is a perspective view for explaining an action of the tube jointing system shown in FIG. 34.

FIG. 38, FIG. 39 and FIG. 40 are perspective views for explaining actions of the tube jointing system 10, respectively.

First, as shown in FIG. 36 and FIG. 37, the connection port manufacturing device 80 is assembled by mounting the cutter unit 802 on the connection port manufacturing device main body 801.

In this case, the flat portion 8021 of the cutter unit 802 is inserted between the projections 8031 and the projections 8033 of the connection port manufacturing device main body 801 from the left side in FIG. 27 and, at the same time, the rib 8026 of the flat portion 8022 is engaged with the groove 8043 of the tube holding section 804. That is, the surface on the lower side in FIG. 37 of the flat portion 8021 of the cutter unit 802 is caused to abut the pair of projections 8031 and 8031 of the connection port manufacturing device main body 801, the surface on the upper side in FIG. 37 of the flat portion 8021 is caused to abut the pair of projections 8033 and 8033, the surface on the lower side in FIG. 37 of the tip portion of the flat portion 8021 is caused to abut an end face 8045 on the upper side in FIG. 37 of the tube holding section 804, the surface on the lower side in FIG. 37 of the flat portion 8022 is caused to abut the pair of projections 8032 and 8032, and the rib 8026 of the flat portion 8022 is engaged with the groove 8043 of the tube holding section 804.

Subsequently, as shown in FIG. 38, the tube 30 is mounted on the tube holding section 804 of the connection port manufacturing device main body 801. In this case, while selecting a predetermined position in the axial direction of the tube 30 (position to which the connector 50 is to be connected) and, at the same time, confirming a position of the inner slit 303 of the tube 30 according to a not-shown guidepost, the tube 30 is mounted such that the inner slit 303 is placed in the central part of the opened portion 8041 of the tube holding section 804.

When the tube 30 is mounted on the tube holding section 804, the tube 30 is held by the tube holding section 804 in a state in which the inner surfaces of the inner slit 303 are brought into press contact with each other, and the tube 30 is prevented from moving with respect to the tube holding section 804 in the axial direction and the peripheral direction thereof.

Subsequently, the cutter unit 802 is moved to the right side in FIG. 37 with respect to the connection port manufacturing device main body 801. In this case, while pressing the flat portion 8021 of the cutter unit 802 toward the lower side in FIG. 37, the flat portion 8021 is moved to the right side in FIG. 37.

Consequently, as shown in FIG. 39, the flat portion 8021 moves to the right side in FIG. 39 (direction perpendicular to the axis of the tube 30) along the projections 8031 of the connection port manufacturing device main body 801 and the end face 8045 of the tube holding section 804 and along side surfaces 8034. The outer slit 307 is formed in the tube 30 by the blade 8025. That is, the connection port 300 is formed.

In this case, a position and a direction of the outer slit 307 are regulated by the flat portion 8021 of the cutter unit 802 and the side surfaces 804 of the connection port manufacturing device main body 801, and a depth of the outer slit 307 is regulated by the flat portion 8021 of the cutter unit 802, the projections 8033 of the connection port manufacturing main body 801 and the end face 8045 of the tube holding section 804. Therefore, regulating means is constituted by these members.

Subsequently, as shown in FIG. 40, the cutter unit 802 is turned by approximately 90° around the curved portion 8023 with respect to the connection port manufacturing device main body 801, and the step portions 8027 of the cutter unit 802 are engaged with the projections 8031 of the connection port manufacturing device main body 801.

Consequently, the cutter unit 802 is held by the connection port manufacturing device main body 801, the vicinity of the connection port 300 of the tube 30 is exposed from the opening 8024 of the cutter unit 802, and the connection port 300 is brought into a state in which the connector 50 can be connected to it.

Since subsequent actions are the same as those in the aforementioned each embodiment, descriptions of the actions will be omitted.

According to this tube jointing system 10, the same effect as the tube jointing system 10 of the aforementioned each embodiment is obtained, for example, the connection port 300 can be formed easily in an arbitrary position.

Further, since this tube jointing system 10 includes the connection-port manufacturing device 80, the outer slit 307 can be formed easily and accurately.

Note that, although a tube holding section of a connection port manufacturing device also serves as a housing in this embodiment, the connection port manufacturing device is not limited to this but may be an instrument dedicated for forming a connection port (outer slit) (which may not have a function as a housing) in the present invention.

The valve element and the mixing and injecting device using the valve element, and the tube, the tube jointing device, the connection port manufacturing device, and the tube jointing system of the present invention have been described so far based on the illustrated each embodiment. However, the present invention is not limited to these, and a structure of each portion can be replaced with an arbitrary structure having the same function.

For example, in the present invention, an arbitrary structure of the aforementioned each embodiment may be combined.

In addition, in the present invention, a shape of the valve element is not limited to a plate-like shape or a tubular shape.

In addition, in the present invention, only a part of the valve element may be constituted by an elastic material.

In addition, an application of the valve element of the present invention is not specifically limited. Examples of the application of the valve element include a mixing and injecting device, a catheter introducer serving as a guiding port in inserting a catheter into a blood vessel, a urethra indwelling catheter, a valve for a balloon as in a Swan-Gantz catheter, and the like. Among them, examples of a preferred application include the mixing and injecting device, and examples of a particularly preferable application include the mixing and injecting device of the present invention.

In addition, a form (type) of a mixing and injecting device to which the valve element of the present invention is applied such as the mixing and injecting device of the present invention is not specifically limited. Examples of the mixing and injecting device include a mixing and injecting port of an infusion set such as an infusion set for drip of a pump type or a gravity type, a mixing and injecting manifold, a Y site, a mixing and injecting and sampling port of a blood circuit for an artificial lung or an artificial kidney, a sampling port of a blood bag, a check valve for preventing backflow of blood when an indwelling needle is retained in a blood vessel, and the like.

In addition, an application of the tube, the tube jointing device, the connection port manufacturing device and the tube jointing system of the present invention is not specifically limited, and examples of the application include, other than a mixing and injecting device or a valve element used for the mixing and injecting device, a discharge port of a liquid container, a mixing and injecting route of a solution to a powder container, and the like. Among them, examples of a preferred application include the mixing and injecting device and the valve element used for the mixing and injecting device, and examples of a particularly preferred application include the valve element of the present invention and the mixing and injecting device of the present invention.

Note that the present invention is not limited to those for medical use.

INDUSTRIAL APPLICABILITY

As described above, according to the valve element of the present invention, liquid tightness is secured and leakage of liquid from the valve element can be prevented surely not only when nothing is inserted in (inserted through) the valve element but also when, for example, a bar-like body such as a hard pipe (tube body) is inserted in the valve element, when a bar-like body of a different external diameter is inserted in the valve element, or when a bar-like body is inserted into and pulled out from the valve element.

In addition, since the valve element is deformed such that the inner surfaces of the second slit are brought into press contact with each other, if a bar-like body is inserted for a long period, the valve element is brought into a liquid tight state surely even after the bar-like body is pulled out, and leakage of liquid from the valve element can be prevented surely.

In addition, since the valve element is deformed such that the inner surfaces of the second slit are brought into press contact with each other, even if width of the first slit or the second slit is made relatively large, leakage of liquid from the valve element can be prevented.

Further, by making the width of the first slit or the second slit relatively large, a frictional resistance at the time of inserting a bar-like body and at the time of pulling it out can be made relatively small. Consequently, operations such as insertion and pulling out of the bar-like body can be performed easily.

In addition, the valve element of the present invention is simple in structure.

In addition, when the valve element is tubular, liquid tightness can be secured more surely, and leakage of liquid from the valve element can be prevented more surely.

In addition, according to the mixing and injecting device of the present invention, for example, when a syringe, a connector or the like is connected, since a bar-like body (e.g., tube body such as a hard pipe) only has to be inserted from the first slit of the valve element, the connecting operation can be performed easily and safely (connection operability is high).

Further, according to the present invention, a connection port (e.g., a mixing and injecting port or the like through which mixing and injection or sampling can be performed) can be manufactured easily, if necessary.

Consequently, various types of flow path circuit formation can be performed.

The invention claimed is:

1. A valve element including a pair of end faces, at least a part of which is constituted by an elastic material, characterized in that, the valve element is provided with a first slit that is opened to a first end face and is not opened to a second end face of the pair of end faces, and a second slit that crosses with the first slit inside the valve element, is opened to the second end face and is not opened to the first end face, and the valve element is deformed such that inner surfaces of the second slit are brought into press contact with each other.

2. A valve element according to claim 1, wherein the first slit in the first end face and the second slit in the second end face are substantially perpendicular to each other.

3. A valve element according to claim 1, wherein the valve element is plate-like, and the inner surfaces of the second slit are brought into press contact with each other by curving the valve element such that the first end face side thereof is protruded.

4. A valve element according to claim 3, wherein a direction of the curving and a direction of the first slit in the first end face substantially coincide with each other.

5. A valve element according to claim 3, wherein a direction perpendicular to the direction of the curving and a direction of the second slit in the second end face substantially coincide with each other.

6. A valve element according to claim 1, wherein the valve element is deformed such that inner surfaces of the first slit are brought into press contact with each other.

7. A valve element according to claim 1, wherein a compressing force is applied to the entire valve element.

8. A valve element according to claim 1, wherein the valve element takes a tubular shape in which the first end face is an external peripheral surface and the second end face is an internal peripheral surface.

9. A valve element according to claim 8, wherein a direction perpendicular to an axial direction of the valve element and a direction of the first slit in the first end face substantially coincide with each other.

10. A valve element according to claim 8, wherein the axial direction of the valve element and a direction of the second slit in the second end face substantially coincide with each other.

11. A valve element according to claim 8, wherein an external shape in a cross section of the valve element after deformation is substantially circular.

12. A valve element according to claim 1, wherein the vicinity of the first slit on the first end face has a flat surface or a recessed surface.

13. A valve element according to claim 1, wherein the valve element includes a holding member for holding the valve element in a deformed state.

14. A mixing and injecting device that includes a valve element according to claim 1 and a housing for holding the valve element and is provided with a flow path in the inside, characterized in that, the valve element includes a first end face exposed to the outside and a second end face exposed to the inside of the flow path, and the valve element is held by the housing in a state in which the valve element is deformed such that inner surfaces of a second slit are brought into press contact with each other.

15. A mixing and injecting device according to claim 14, wherein a direction of the flow path and a direction of the second slit in the second end face substantially coincide with each other.

16. A mixing and injecting device according to claim 14, wherein the valve element takes a tubular shape in which the second end face is an external peripheral surface and the second end face is an internal peripheral surface, and at least a part of the flow path is constituted by a lumen of the valve element.

17. A mixing and injecting device according to claim 16, wherein the valve element is deformed by being compressed in a direction substantially perpendicular to an axial direction of the valve element by the housing.

18. A mixing and injecting device according to claim 16, wherein:

the housing is tubular and has an opening on a side thereof, and a first slit is located in the opening;

the valve element is inserted in the housing; and the mixing and injecting device is constituted such that, when the opening is viewed from a direction of a straight line that passes a position deviated by 90° around a central axis of the valve element from a crossing section where the first slit and the second slit cross with each other and is perpendicular to the axial direction of the valve element, a part of the external peripheral surface of the valve element is seen from the opening.

19. A mixing and injecting device according to claim 16, wherein the housing includes a portion higher than an outer surface of a part where the first slit of the valve element exists, on an external peripheral side of the valve element and in the vicinity of the first slit.

20. A mixing and injecting device according to claim 16, wherein the housing includes a portion, which surrounds a part where the first slit of the valve element exists and is higher than an outer surface of the part where the first slit exists, on an external peripheral side of the valve element and in the vicinity of the first slit.

21. A mixing and injecting device according to claim 16, wherein engaging means for engaging the housing with the valve element is provided.

22. A mixing and injecting device according to claim 16, wherein the valve element is bent such that the lumen thereof is formed in a V-shape.

23. A mixing and injecting device according to claim 22, wherein a crossing section where the first slit and the second slit cross with each other is substantially linear, a direction of the crossing section and an axial direction of the lumen on one side from a bent portion of the valve element substantially coincide with each other, and the lumen on one side is located on an extended line of the crossing section.

24. A mixing and injecting device according to claim 22, wherein a crossing section where the first slit and the second slit cross with each other is substantially linear, and the crossing section and a central axis of the lumen on one side from a bent portion of the valve element substantially coincide with each other.

25. A mixing and injecting device according to claim 14, wherein the vicinity of the first slit on the first end face has a flat surface or a recessed surface.

* * * * *